United States Patent
Wang et al.

(10) Patent No.: US 10,246,726 B2
(45) Date of Patent: Apr. 2, 2019

(54) PHOTOSYNTHETIC PRODUCTION OF 3-HYDROXYBUTYRATE FROM CARBON DIOXIDE

(71) Applicant: ARIZONA BOARD OF REGENTS ON BEHALF OF ARIZONA STATE UNIVERSITY, Scottsdale, AZ (US)

(72) Inventors: Bo Wang, Tempe, AZ (US); Weiwen Zhang, Chandler, AZ (US); Deirdre Meldrum, Phoenix, AZ (US); David Nielsen, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/938,742

(22) Filed: Mar. 28, 2018

(65) Prior Publication Data

US 2018/0312884 A1 Nov. 1, 2018

Related U.S. Application Data

(63) Continuation of application No. 14/479,893, filed on Sep. 8, 2014, now Pat. No. 9,944,955, which is a continuation of application No. PCT/US2013/029997, filed on Mar. 8, 2013.

(60) Provisional application No. 62/017,650, filed on Jun. 26, 2014, provisional application No. 61/646,807, filed on May 14, 2012.

(51) Int. Cl.
| | |
|---|---|
| *C12N 9/04* | (2006.01) |
| *C12N 9/10* | (2006.01) |
| *C12N 9/16* | (2006.01) |
| *C12P 7/52* | (2006.01) |
| *C07C 59/01* | (2006.01) |

(52) U.S. Cl.
CPC .............. *C12P 7/52* (2013.01); *C07C 59/01* (2013.01); *C12N 9/0006* (2013.01); *C12N 9/1029* (2013.01); *C12N 9/16* (2013.01); *C12Y 101/01036* (2013.01); *C12Y 101/01157* (2013.01); *C12Y 203/01009* (2013.01); *C12Y 301/0202* (2013.01)

(58) Field of Classification Search
None
See application file for complete search history.

(56) References Cited

U.S. PATENT DOCUMENTS

2009/0155869 A1 6/2009 Buelter et al.
2010/0255549 A1 10/2010 Martin et al.

OTHER PUBLICATIONS

Liu X et al. Fatty acid production in genetically modified cyanobacteria. 2011. Proceedings of the National Academy of Sciences. vol. 108, No. 17. p. 6899-6904.*

Tseng H et al. Metabolic Engineering of *Escherichia coli* for Enhanced Production of (R)- and (S)-3-hydroxybutyrate. 2009. Applied and Environmental Microbiology. vol. 75, No. 10. p. 3137-3145.*

Tseng et al. Metabolic engineering of *Escherichia coli* for enhanced production of (R)—and (S)-3-hydroxybutyrate. Appl. Environ. Microbial. May 2009 (May 2009), vol. 75, No. 10, pp. 3137-3145; abstract; Figs. 1-2; p. 3139, para 5; Table 2.

Knoop et al. The metabolic network of *Synechocystis* sp. PCC 6803: systemic properties of autotrophic growth. Plant Physiol. Sep. 2010 (Sep. 2010), vol. 154, No. 1, pp. 410-422; p. 410, para 1-2; p. 413, para 6—p. 414, para 1.

Wu et al. Accumulation of poly-beta-hydroxybutyrate in *Cyanobacterium synechocystis* sp. PCC6803. Bioresour. Technol. Jan. 2001 (Jan. 2001), vol. 76, No. 2, pp. 85-90.

Tyo et al. Identification of gene disruptions for increased poly-3-hydroxybutyrate accumulation in *Synechocystis* PCC 5803. Biotechnol. Prog. Sep.-Oct. 2009 (Sep.-Oct. 2009), vol. 25, No. 5, pp. 1236-1243.

Tyo et al. High-throughput screen for poly-3-hydroxybutyrate in *Escherichia coli* and *Synechocystis* sp. strain PCC6803. Appl. Environ. Microbial. May 2006 (May 2006), vol. 72, No. 5, pp. 3412-3417.

Liu et al. Microbial production of R-3-hydroxybutyric acid by recombinant *E coli* harboring genes of phbA, phbB, and tesB. Appl. Microbiol. Biotechnol. Sep. 2007 (Sep. 2007), vol. 76, No. 4, pp. 811-818.

Lee et al. Metabolic engineering of *Escherichia coli* for production of enantiomerically pure (R) -(--)-hydroxycarboxylic acids. Appl. Microbiol. Biotechnol. Jun. 2003 (Jun. 2003), vol. 69, No. 6, pp. 3421-3426.

Panda et al. Enhanced poly-beta-hydroxybutyrate accumulation in a unicellular *Cyanobacterium Synechocystis* sp. PCC 6803. Lett. Appl. Microbial. Feb. 2007 (Feb. 2007), vol. 44, No. 2, pp. 194-198.

Photoautotrophs definition (last viewed on Mar. 6, 2017).

(Continued)

*Primary Examiner* — Paul J Holland
(74) *Attorney, Agent, or Firm* — Gavin J. Milczarek-Desai; Quarles & Brady LLP

(57) ABSTRACT

Construction and expression of synthetic pathways to produce (S) or (R)-3-hydroxybutyrate (3HB) as enantiomerically-pure products by genetically engineering cyanobacterium *Synechocystis* sp. PCC 6803. Under optimized growth conditions, the pathway employing phaA and phaB from *R. eutropha* was the most effective, producing up to 533.4±5.5 mg/l (R)-3HB after 21 days photosynthetic cultivation. For the first time, the feasibility and high efficiency of producing 3HB using solar energy and $CO_2$ as sole energy and carbon sources by engineered cyanobacteria is demonstrated.

9 Claims, 18 Drawing Sheets

Specification includes a Sequence Listing.

(56) References Cited

OTHER PUBLICATIONS

Liu et al., Fatty acid production in genetically modified *Cyanobacteria*., PNAS (Apr. 26, 2011), vol. 108(17), pp. 6899-6904.
Osanai et al., Genetic Engineering of Group 2 σ Factor SigE Widely Activates Expressions of Sugar Catabolic Genes in *Synechocystis* Species PCC 6803., The Journal of Biological Chemistry (Sep 11, 2011), vol. 286(35), pp. 30962-30971.
Acetyl Coenzyme A (Molecular Biology), last viewed on Sep. 1, 2016, pp. 1-5.
Gluconeogenesis, last viewed on Sep. 1, 2016, pp. 1-2.
Berry et al., Electron Transport Routes in Whole Cells of *Synechocystis* sp. Strain PCC 6803: The Role of the Cytochrome bd-Type Oxidase., Biochemistry, 2002, vol. 41 (10), pp. 3422-3429.
Taroncher-Oldenburg et al., Identification and Analysis of the Polyhydroxyalkanoate-Specific β-Ketothiolase and Acetoacetyl Coenzyme A Reductase Genes in the *Cyanobacterium synechocystis* sp. Strain PCC6803., Appl. Environ. Microbiol. (2000), vol. 66(10), pp. 4440-4448.
Wacey et al., Disentangling the perturbational effects of amino acid substitutions in the DNA-binding domain of p53., Hum Genet, 1999, vol. 104, pp. 15-22.
Guo et al., Protein tolerance to random amino acid change, 2004, Proc. Natl. Acad. Sci. USA 101: 9205-9210.
Lazar et al., Transforming Growth Factor α: Mutation of Aspartic Acid 47 and Leucine 48 Results in Different Biological Activity, 1988, Mol. Cell. Biol. 8:1247-1252.
Hill et al., Functional Analysis of conserved Histidines in ADP-Glucose Pyrophosphorylase from *Escherichia coli*, 1998, Biochem. Biophys. Res. Comm. 244:573-577.
Patent Cooperation Treaty, International Searching Authority, International Preliminary Report on Patentability for PCT/US2013/029997, 5 pages, dated Nov. 18, 2014.

\* cited by examiner

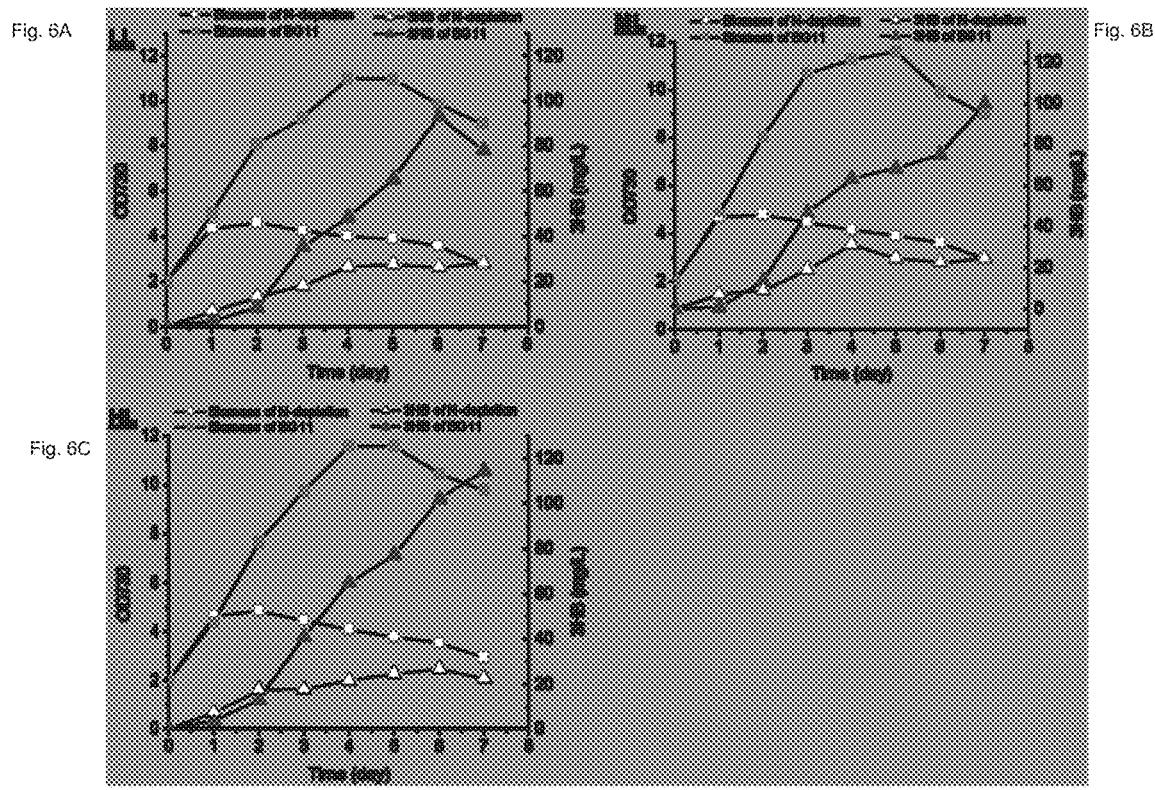

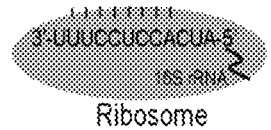
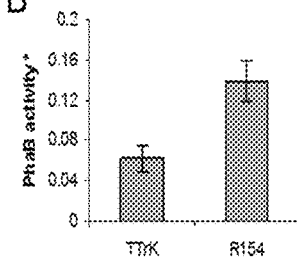
Fig. 18A
SEQ ID NO. 3    Original RBS:    AAGGAGTGGAC + ATG
SEQ ID NO. 4    Optimized RBS:   AAGGAGGTAAC + ATG
SEQ ID NO. 5
Fig. 18B
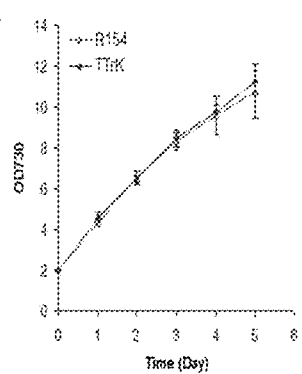
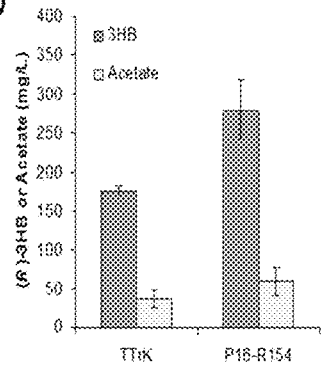
Fig. 18C
Fig. 18D
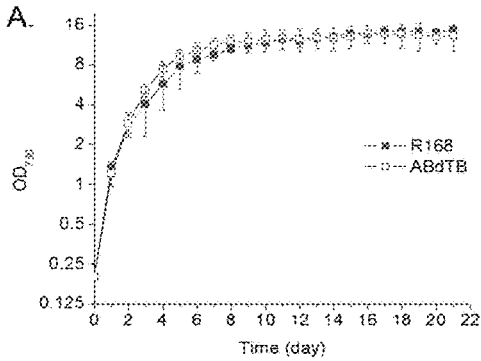
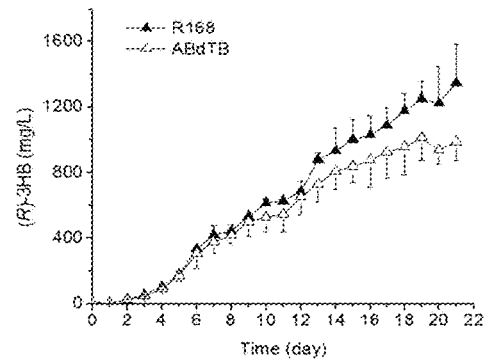
Fig. 19A
Fig. 19B

SEQUENCE LISTING

```
<160> NUMBER OF SEQ ID NOS: 5

<210> SEQ ID NO 1
<211> LENGTH: 82
<212> TYPE: DNA
<213> ORGANISM: Artificial Sequence
<220> FEATURE:
<223> OTHER INFORMATION: Synthetic primer

<400> SEQUENCE: 1
gagctgttga caattaatca tcggctcgta taatgtgtgg aattgtgagc ggataacaat    60
ttcacacaag gaggatatac at                                            82

<210> SEQ ID NO 2
<211> LENGTH: 180
<212> TYPE: DNA
<213> ORGANISM: Artificial Sequence
<220> FEATURE:
<223> OTHER INFORMATION: Synthetic primer

<400> SEQUENCE: 2
gccctctgtt tacccatgga aaaaacgaca attacaagaa agtaaaactt atgtcatcta    60
taagcttcgt gtatattaac ttcctgttac aaagctttac aaaactctca ttaatccttt   120
agactaagtt tagtcagttc caatctgaac atcgacaaat acataaggaa ttataaccaa   180

<210> SEQ ID NO 3
<211> LENGTH: 11
<212> TYPE: DNA
<213> ORGANISM: Artificial Sequence
<220> FEATURE:
<223> OTHER INFORMATION: Synthetic primer

<400> SEQUENCE: 3
aaggagtgga c                                                        11

<210> SEQ ID NO 4
<211> LENGTH: 11
<212> TYPE: DNA
<213> ORGANISM: Artificial Sequence
<220> FEATURE:
<223> OTHER INFORMATION: Synthetic primer

<400> SEQUENCE: 4
aaggaggtaa c                                                        11

<210> SEQ ID NO 5
<211> LENGTH: 12
<212> TYPE: RNA
<213> ORGANISM: Artificial Sequence
<220> FEATURE:
<223> OTHER INFORMATION: 16s rRNA binding site

<400> SEQUENCE: 5
uuuccuccac ua                                                       12
```

PHOTOSYNTHETIC PRODUCTION OF 3-HYDROXYBUTYRATE FROM CARBON DIOXIDE

CROSS-REFERENCE TO RELATED APPLICATIONS

This Application is a continuation of U.S. patent application Ser. No. 14/479,893, filed on Sep. 8, 2014, which claims the benefit of U.S. Provisional Patent Application No. 62/017,650, filed on Jun. 26, 2014, and is a continuation of International Application No. PCT/US2013/029997, filed on Mar. 8, 2013, which claims the benefit of U.S. Provisional Patent Application No. 61/646,807, filed on May 14, 2012, the disclosures of each patent or patent application are incorporated by reference herein in their entirety.

BACKGROUND OF THE INVENTION

Although human society has progressed significantly over past centuries through the development and use of petroleum-derived products (e.g. fuels, plastics, solvents, etc.), their over-utilization has caused environmental issues including increasing atmospheric concentration of $CO_2$ (a greenhouse gas), pollution from petrochemical production and use, and disposal of non-biodegradable plastic materials. More importantly, petroleum resources are finite and not renewable in nature. For these reasons it is necessary to seek alternative approaches to produce fuels and chemicals using renewable resources. Photosynthetic cyanobacteria have attracted significant attention in recent years as a 'microbial factory' to produce biofuels and chemicals due to their capability to utilize solar energy and $CO_2$ as the sole energy and carbon sources, respectively.

Lipid-rich cyanobacteria and microalgae have most notably been employed to produce fuels such as biodiesel. Cyanobacteria are also natural producers of the naturally-occurring biodegradable plastic poly-β-hydroxybutyrate (PHB). Despite efforts to enhance PHB biosynthesis through both genetic engineering strategies and the optimization of culture conditions, PHB biosynthesis by cyanobacteria was a multi-stage cultivation process that involved nitrogen starvation followed by supplementation of fructose or acetate, which does not capitalize on the important photosynthetic potential of cyanobacteria. Most importantly, as neither lipids nor PHB are secreted by the cells, the required processes for their extraction are energy-intensive and remain as one of the major hurdles for commercial applications. As a result, researchers have recently focused on engineering cyanobacteria to instead produce secretable biofuels and chemicals. However, most production titers are below 200 mg/l and to our knowledge no report demonstrated the potential of employing photosynthetic microorganisms in a continuous production process.

SUMMARY OF THE INVENTION

Different from PHB, which accumulates inside cells, 3-hydroxybutyrate (3HB) is a small molecule that could possibly be secreted out of the cells into extracellular environment, thereby facilitating its collection. 3HB can then be chemo-catalytically polymerized to produce PHB or be co-polymerized with other organic acid compounds to synthesize renewable plastics with a broader range of chemical and material properties (including adjustable molecular weight and improved purity) relative to naturally-synthesized PHB. (R)- or (S)-3HB can also serve as a precursor for many stereo-specific fine chemicals such as antibiotics, pheromones and amino acids. Moreover, (R)-3HB has been found to be an advanced nutrition source for tissue cells and can reduce the death rate of the human neuronal cells, improve mice memory and promote growth of osteoblasts.

3HB synthetic pathways in cyanobacterium *Synechocystis* sp. PCC 6803 (hereafter *Synechocystis* 6803) were constructed and demonstrated highly efficient photosynthetic production and secretion of 3HB using solar energy and $CO_2$ as the sole carbon and energy sources. Thus, multi-cycle or continuous production of 3HB from engineered *Synechocystis* are possible.

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

BRIEF DESCRIPTION OF THE FIGURES

FIGS. 6A-C depict *Synechocystis* TAB1 cells subjected to nitrogen starvation and normal BG11 medium (control) cultures. Overall, higher 3HB production and cell density of the control versus that of the nitrogen-starved counterparts was observed.

FIG. 18A-D are optimizations of the RBS for gene phaB1 in *Synechocystis* strain R154. (A) The original and optimized ribosome binding site. (B) Acetoacetyl-CoA reductase activity. (C) Cell growth curve of strains TTrK and R154. (D) Production of (R)-3HB and acetate.

FIGS. 19A-B show photosynthetic production of (R)-3HB from $CO_2$ by *Synechocystis* strain R168. (A) Cell growth curve of strains R168 and ABdTB. (B) Time course of in-flask (R)-3HB generated by strains R168 and ABdTB.

DETAILED DESCRIPTION OF THE INVENTION

Figure 1:
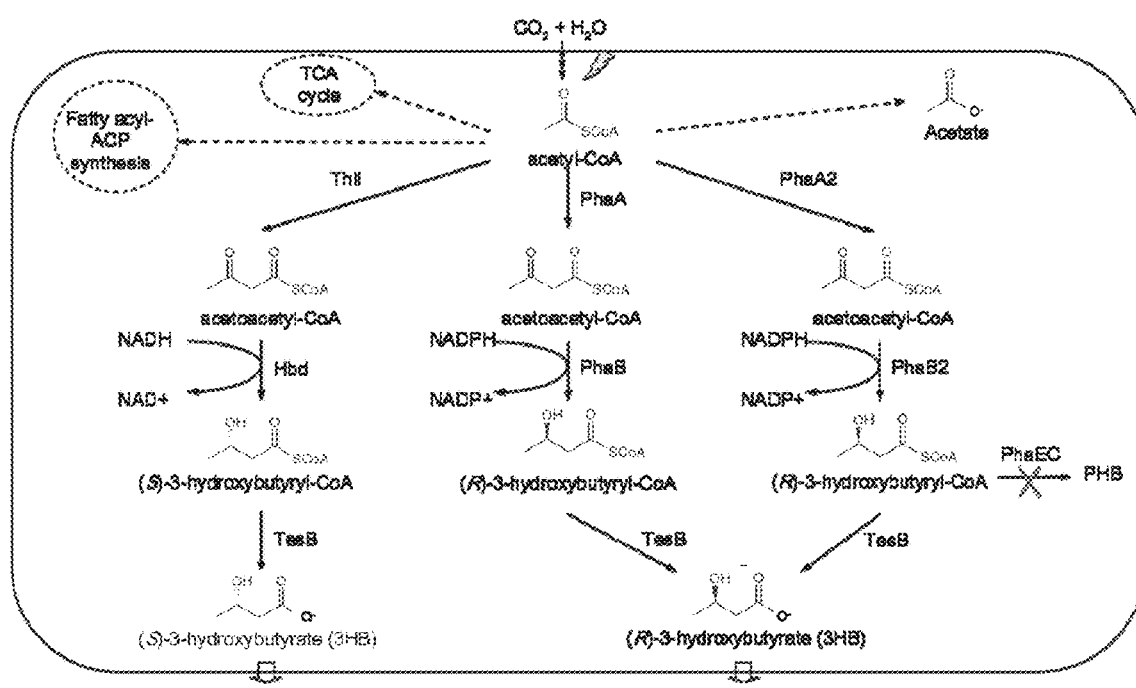
FIG. 1 is a schematic representation of (S)-3HB and (R)-3HB biosynthesis from $CO_2$ in engineered *Synechocystis*. Thil, thiolase from *C. acetobutilicum* ATCC824; PhaA, thiolase from *R. eutropha* H16; PhaA2 (Slr1993), native thiolase in *Synechocystis* 6803; Hbd (S)-3-hydroxybutyryl-CoA dehydrogenase from *C. acetobutilicum* ATCC824; PhaB, (R)-3-hydroxybutyryl-CoA dehydrogenase from *R. eutropha* H16; PhaB2 (Slr1994), native (R)-3-hydroxybutyryl-CoA dehydrogenase in *Synechocystis* 6803; TesB, thioesterase II from *E. coli* XL1-Blue MRF'; PhaEC, native PHB polymerase in *Synechocystis* 6803.

In a first aspect, this disclosure relates to engineered strains of *Synechocystis*. 3HB synthetic pathways in cyanobacterium *Synechocystis* 6803 were constructed and demonstrated highly efficient photosynthetic production of 3HB using solar energy as the sole energy source.

In a second aspect, this disclosure relates to highly efficient photosynthetic production of 3HB using bicarbonate or $CO_2$ as the sole carbon source by engineered *Synechocystis*.

In a third aspect, this disclosure relates to biosynthesis of 3HB in a process coupled with oxygenic photosynthesis in engineered *Synechocystis*.

In a fourth aspect, this disclosure relates to highly efficient secretion of hydrophilic 3HB molecules by engineered *Synechocystis* without overexpression of specific transporters.

In a fifth aspect, this disclosure relates to multi-cycle or continuous photosynthetic production of 3HB from engineered *Synechocystis*.

In a sixth aspect, this disclosure relates to photosynthetic production of 3HB from engineered cyanobacteria.

While the embodiments described below utilize *Synechocystis*, those of ordinary skill will appreciate that other cyanobacterial species may be engineered to produce 3HB following the strategies and genetic engineering guidance provided herein. Therefore, this disclosure is not limited to 3HB production from *Synechocystis* but rather extends to 3HB production from all cyanobacteria capable of genetic manipulation of 3HB biosynthesis pathways.

Construction and expression of synthetic pathways to produce (S) or (R)-3-hydroxybutyrate (3HB) as enantiomerically-pure products using cyanobacterium *Synechocystis* sp. PCC 6803 was undertaken as described below. However, this disclosure is not limited to the exact methods and materials described.

*Synechocystis* Strains and Culture Conditions.

A series of *Synechocystis* strains were constructed using marker modification and markerless modification methods. *Synechocystis* 6803 and its derivatives were grown in BG11 medium under a light intensity of 35 $\mu E/m^2/s$ unless otherwise specified. For BG11 plates for *Synechocystis* growth, 10 mM TES (pH 8.2), 3 g/l thiosulfate and 1.5% agar was supplemented before autoclaving. *E. coli* XL1-Blue MRF' (Stratagene, La Jolla, Calif.) was used as host to construct and store all recombinant plasmids. All strains of *E. coli* were cultivated in Luria-Bertani (LB) medium at 37° C. Antibiotics were supplemented as appropriate at the following concentrations: 100 ng/l ampicillin, 30 ng/μl kanamycin, and 25 ng/μl chloramphenicol. *Bacillus subtilis* strain 168 was obtained from American Type Culture Collection (ATCC) and was cultured in LB medium at 30° C.

*Synechocystis* 6803 genomic DNA was purified by DNeasy Blood & Tissue Kit (QIAGEN, Valencia, Calif.) and subsequently used as template for PCR amplification of SR12 (slr1495) and SL12 (sll1397) DNA fragments. SR12 and SL12 were recombined together by overlapping PCR and were inserted into the SacI and KpnI restriction sites of the plasmid pBluescript II SK(+) (Stratagene, La Jolla, Calif.) to construct pBS-SRSL. From the genomic DNA of *Clostridium acetobutylicum* ATCC 824, thil gene was PCR amplified using primers Th5 and Th8. The purified product was then again PCR amplified by primers Ptac and Th8 to construct Ptac-thil, wherein thil was under the control of the Ptac promoter. The gel-purified Ptac-thil product was then again PCR amplified using primers TAC5 and Th8, the product of which was purified and restriction digested before being inserted into the BamHI and SalI sites of pBS-SRSL to construct pBS-SPT. Next, hbd of *C. acetobutylicum* was PCR amplified with primers HBD3 and HBD6. The resultant fragment was purified and restriction digested before being inserted between the NcoI and SalI sites of pBS-SPT to construct pBS-SPTH. Two fragments of the cat ($Cm^R$) gene on pACYC 184 (New England Biolabs, Ipswich, Mass.) were amplified using primer pairs Cat3 and Cat4, Cat5 and Cat6, and then were recombined by overlapping PCR using primers Cat3 and Cat6 to remove the NcoI restriction site in the open reading frame. The NcoI-removed cat gene was then inserted between the PstI and BamHI sites of pBS-SRSL to construct pBS-SCat. The Ptac-thil-hbd fragment of pBS-SPTH was PCR amplified using primers TAC5 and HBD6 and then inserted between the BamHI and SalI sites of pBS-SCat to construct pBS-SCPTH. The Ptac-thil fragment from pBS-SCPTH was PCR amplified using primers TAC5 and primer Th10 and was used to replace the original Ptac-thil fragment of pBS-SCPTH between BamHI and NcoI to construct pBS-SCPTH2. The R. eutropha H16 gene phaB was PCR amplified with primers PHAB11 and PHAB12 using pETphaAphaB (reconstructed based on the methods of Tseng et al. in constructing pET-P-P) as template and was inserted between the MluI and HindIII sites of pBS-SCPTH2 to construct pBS-SCPTB. The gene phaA from R. eutropha H16 was PCR amplified using primers PHAA11 and PHAA12 with pETphaAphaB as template. The purified product was then amplified using primers Ptac and primer PHAA12 to construct the Ptac-phaA fragment. Ptac-phaA was further PCR amplified using primers TAC5 and PHAA12 before being inserted between the BamHI and MluI sites of pBS-SCPTB to construct pBS-SCPAB.

The DNA fragment containing GTP from Synechocystis 6803 was PCR amplified using primers GTP1 and GTP2 and was inserted between the SacI and PstI sites of pBS-SCat to construct pBS-SCG. The DNA fragment PHAU from Synechocystis 6803 was PCR amplified using primers PHAU1 and PHAU2 before being further PCR amplified using primers Ptac and PHAU2 to construct Ptac-PHAU. Ptac-PHAU was then amplified using primers TAC5 and PHAU2 and the product was inserted between the BamHI and KpnI sites of pBS-SCG to construct pBS-GCPU.

The DNA fragments SR56 and SL56 were PCR amplified using primer pairs SR5 and SR6 and SL5 and SL6 with Synechocystis 6803 genomic DNA as template. Fragments SR56 and SL56 were recombined together by overlapping PCR before being inserted into the SacI and XhoI restriction sites of the plasmid pBluescript II SK(+) to construct pBS-S2. pBS-S2 was digested with MluI and SalI before being ligated with kan ($Kan^R$) which was amplified from pET-30a (+) (Novagen, Madison, Wis.) using primers Kan1 and Kan2 to construct pBS-S2K. The E. coli gene tesB was amplified with primers TESB1 and primer TESB2 using the E. coli XL1-Blue MRF' genomic DNA as template. Ptac promoter was PCR amplified with primers TAC11 and TACTESB1 using pBS-SPTH as template. The Ptac and tesB containing PCR products were then recombined by overlapping PCR using primers TAC11 and TESB2 to construct the fragment Ptac-tesB. Ptac-tesB was digested with BglII and HindIII before being inserted between the corresponding sites of pBS-S2K to construct pBS-SPtTeK.

The DNA fragment PpasD56 was PCR amplified from the Synechocystis 6803 genomic DNA using primers PpsaD5 and PpsaD6. The thil gene was PCR amplified from C. acetobutylicum ATCC 824 genomic DNA using primers Th1 and Th2. The PCR product was recombined with PpsaD56 by overlapping PCR using primers PpsaD5 and Th2 and the resultant PpsaD-thil product was inserted between the BamHI and MluI sites of pBS-S2K to construct pBS-SPTK. Ptac was amplified from pBS-SPTH using primers TAC5 and TAC-PTB3 and then inserted between the BamHI and NdeI sites of pBS-SPTK to construct pBS-SPtK. The sacB gene was PCR amplified using primers SACB8 and SACB9 using B. subtillus genomic DNA as template. The product was restriction digested and inserted between the NdeI and MluI sites of the pBS-SPtK plasmid to construct pBS-SPSK2. DNA fragments PHA1 and PHA2 were each PCR amplified from Synechocystis 6803 genomic DNA using primer pairs PHA11 and PHA12 and PHA21 and PHA22. Fragments PHA1 and PHA2 were then recombined together by overlapping PCR using primers PHA11 and PHA22 to construct the DNA fragment PHA. PHA was then inserted between the XhoI and SacI sites of pBS-S2 to construct pBS-PHA. The Ptac-sacB-kan fragment was removed from pBS-SPSK2 by digestion with BamHI and SalI and then inserted between the corresponding sites of pBS-PHA to construct pBS-SPSK3.

Modification of Synechocystis Genome.

Synechocystis strains were grown to an $OD_{730}$ of 0.2-0.4, at which time point 0.5 ml culture was pelleted by centrifugation at 2700×g for 10 min at room temperature. The cell pellet was re-suspended in 50 µl fresh BG11 medium to which approximately 2 µg of the chromosome-targeting plasmid was added and mixed. The mixture was incubated at 30° C. under light (~25 $\mu E/m^2/s$) for 5 h before being plated on BG11 solid agar plates with appropriate antibiotics supplements, 10 ng/µl kanamycin or 5 ng/µl chloramphenicol. The plates were placed at 30° C. under light and colonies could be seen within two weeks. Individual colonies were then isolated and re-streaked on BG11 solid agar plates with appropriate antibiotics for additional one to two weeks to achieve full chromosome segregation, as was verified by colony PCR. Alternatively, markerless modification of the Synechocystis genome was conducted using the method described previously with minor modifications.

Briefly, fragment Ptac-sacB-kan was inserted into the neutral site of Synechocystis 6803 using a marker modification method as described in the text. After confirming that the resultant strain was genotypically pure as verified using colony PCR, the strain were grown in BG11 medium to an $OD_{730}$ of 0.2-0.4, when cells were centrifuged at 2700×g for 10 min at room temperature and was resuspended to $OD_{730}$ of 4.0 by 50 µl BG11. About 2 µg of chromosome-targeting plasmid pBS-PHA was added and mixed well with the cells. The mixture was incubated at 30° C. under light (25 $\mu E/m^2/s$) for 5 h before being transferred into 25 ml BG11 medium in a 50 ml flask. Cells were then further cultivated for 4-5 days after which about $1.3 \times 10^8$ cells (assuming $OD_{730}$ of 0.6 equals to $10^8$ cells/ml) were spread onto a BG11 plate containing 4.5% (w/v) sucrose for counter-selection. The plates were incubated at 30° C. under light for one or two weeks before colonies appeared. Individual colonies were then re-streaked on fresh BG11 plates with 4.5% sucrose for additional one to two weeks until full chromosome segregation was achieved, as verified by colony PCR.

Gene Expression Analysis:

Synechocystis strains were inoculated in 50 ml flasks, each containing 10 ml BG11 (10 mM TES-NaOH), to an initial $OD_{730}$ of 1.5. Then cells were incubated in a shaking bed (150 rpm) at 30° C. with light intensity of 35 $\mu E/m^2/s$ for 5 days. Every 24 h, 0.5 ml 1.0M $NaHCO_3$ was added to each culture and the pH of the culture medium was adjusted to 7.5 by addition of 10 N HCl.

RT-qPCR.

Approximately 1.67×10 Synechocystis cells (assuming $OD_{730}$ of 0.6 equals to $10^8$ cells/ml) were collected by centrifugation at 17,000×g, 4° C. for 1 min. The supernatant was discarded and the cell pellet was kept under −80° C. until RNA extraction. Total RNA extraction, cDNA synthesis and RT-qPCR were conducted using methods described previously.

Enzyme Activity Assay.

3.3×10' cells were collected by centrifugation at 5000×g at 4° C. for 10 min. The supernatant was discarded and the cell pellet was used either immediately or frozen at −80° C.

for assaying at a later date. For all enzyme assays, the cell pellet was first re-suspended in 1.0 ml 100-mM Tris-HCl (pH7.5) and then subjected to sonication in ice bath using a Branson Digital Sonifier Model 102C CE (Branson Ultrasonics, Danbury, Conn.) and Sonic Dismembrator Model 500 (Fisher Scientific, Waltham, Mass.) to lyse cells. The sonication program consisted of: 3-sec-on/3-sec-off for 100 cycles. Cellular debris was removed by centrifugation at 17,000×g at 4° C. for 10 min. The resultant supernatant was used for enzyme assays.

The thiolase (encoded by phaA2, phaA or thil) activity was determined using acetoacetyl-CoA and CoA as substrates. The decrease in absorbance at 303 nm was monitored as function of time and specific enzyme activity was calculated by using a molar extinction coefficient of 14,000 $M^{-1}cm^{-1}$. The activity of (R)-3-hydroxybutyryl-CoA dehydrogenase (encoded by phaB2 or phaB) was determined using acetoacetyl-CoA and NADPH as substrates. The activity of (S)-3-hydroxybutyryl-CoA dehydrogenase (encoded by hbd) was determined using acetoacetyl-CoA and NADH as substrates. The decrease in absorbance at 340 nm was monitored over time and specific enzyme activity was calculated by using a molar extinction coefficient of 6,220 $M^{-1}cm^{-1}$. The thioesterase activity was determined using butyryl-CoA, decanoyl-CoA or acetyl-CoA as substrate and the release of CoA was monitored at 412 nm by using 5,5'-dithiobis(2-nitrobenzoic acid) (DTNB; Sigma-Aldrich, St. Louis, Mo.). The molar extinction coefficient was taken as 13,600.

Thioesterase (TesB) Activity Specificity Assay.

The thioesterase activities were examined using different acyl-CoA substrates including decanoyl-CoA (10 carbon acyl group), butyryl-CoA (4 carbon acyl group) and acetyl-CoA (2 carbon acyl group). The release of CoA was monitored at 412 nm by using 5,5'-dithiobis(2-nitrobenzoic acid) (DTNB; Sigma-Aldrich, St. Louis, Mo.). The molar extinction coefficient was taken as 13,600.

For TesB assay in Synechocystis, 20 $OD_{730}$·mL Synechocystis strain TESB cells was collected after 5 days cultivation. The cell pellet was first re-suspended in 1.0 ml 100-mM Tris-HCl (pH7.5) and then subjected to sonication in ice bath using a Branson Digital Sonifier Model 102C CE (Branson Ultrasonics, Danbury, Conn.) and Sonic Dismembrator Model 500 (Fisher Scientific, Waltham, Mass.) to lyse cells. The sonication program consisted of: 3-sec-on/3-sec-off for 100 cycles. Cellular debris was removed by centrifugation at 17,000×g at 4° C. for 10 min. The resultant supernatant was used for enzyme assays using same molar concentration of different acyl-CoA substrates.

For TesB assay in E. coli, strain XL1-Blue/pBS-SPtTeK cells was collected after ~10 hours cultivation in a 50 ml tube containing 10 ml LB medium at 37° C., 200 rpm. After 10 h cultivation, the $OD_{600}$ of E. coli XL1-Blue/pBS-SPtTeK and E. coli XL1-Blue/pBS-S2K was 5.3 and 4.6, respectively, and thus 3.8 ml and 4.4 ml culture was pelletied for each before sonication. The cells were lysed using same method as described above. The resultant supernatant was used for enzyme assays using same molar concentration of butyryl-CoA and acetyl-CoA as substrates. E. coli XL1-Blue/pBS-S2K was used as a control in these enzyme assays.

3HB Production.

Each strain was inoculated into 20 ml BG11 medium in a 50 ml flask at an initial $OD_{730}$ of 0.1, and then grown photosynthetically to an $OD_{730}$ of 0.5-1.0 before $NaHCO_3$ was then added to a final concentration of 50 mM. When the cell density reached an $OD_{730}$ of 1.0-2.0, cells were collected by centrifuging at 5000×g for 10 min at 20° C. Cell pellets were re-suspended in 10 ml of fresh BG11 containing 50 mM $NaHCO_3$ in 50 ml flasks to a cell density of an $OD_{730}$ of 1.5. The pH of the medium was adjusted to 7.5. The re-suspended cells were then incubated in a shaking bed (150 rpm) at 30° C. with light intensity of 35 $\mu E/m^2/s$ for 5 days. Every 24 h, 0.5 ml 1.0M $NaHCO_3$ was added to each culture and the pH of the culture medium was adjusted to 7.5 by addition of 10 N HCl. All culture experiments were conducted in triplicate for each strain.

Nitrogen Limitation Test.

Synechocystis TABd was grown to an $OD_{730}$ of 1.0-2.0 as described above before the cells were pelleted and collected. Cell pellets were re-suspended in 10 ml BG11 containing 10 mM TES-NaOH (pH8.0) and 50 mM $NaHCO_3$ in 50 ml-flasks with an initial cell density of $OD_{730}$ of 2.0. The initial pH of culture medium was adjusted to 7.5 by adding 10 N HCl. Once daily, 1 ml of the culture was sampled for analysis and replaced with 1 ml fresh BG11 containing 500 mM $NaHCO_3$ and 1.5 g/l, 0.75 g/11 and none of $NaNO_3$, as appropriate. Thus, 50 mM fresh $NaHCO_3$ and either 10%, 5% or 0% of fresh $NaNO_3$ were added to the culture medium each day (corresponding to 10%-N, 5%-N or non-N culture, respectively).

Production of 3HB by Intermittent Medium Exchange.

After 10 days cultivation (Cycle I) using the 5%-N supplementation strategy as stated above, Synechocystis TABd cells were collected and re-suspended in 10 ml fresh BG11-10N (10 mM TES-NaOH, pH8.0) medium that contained only 10% of the $NaNO_3$ content in typical BG11 medium to re-initiate cultivation in 50 ml flasks for a second 10 days (days 11 through 20; called Cycle II). During this period, 250 μl of cell culture was sampled for analysis each day. After sampling, 250 μl fresh BG11 medium, 10 μl 37.5 g/11 $NaNO_3$ (equivalent to the nitrate content of 250 μl BG11) and 250 μl 2.0 M $NaHCO_3$ were added back into the culture. Note that since evaporative water losses from the culture were calculated to be about 260 μl per day, the above supplementation protocol was used to maintain the total culture volume. This protocol resulted in the daily addition of 5% of the $NaNO_3$ to the culture medium.

Photosynthetic 3HB production from $CO_2$. Synechocystis was inoculated into a 125 ml flask containing 75 ml autoclaved BG11 (10 mM TES-NaOH) medium to an initial $OD_{730}$ of 0.2. The culture was placed at 30° C. with continuous illumination of 120 $\mu E/m^2/s$ and was bubbled with ambient air. The aeration rate was initially set as 75 ml/min. When the culture $OD_{730}$ surpassed about 0.6, the aeration rate was then increased to 250 ml/min. Daily, 1 ml of culture was sampled and 1 ml 5-fold concentrated sterilized BG11 medium was added back into the culture until day 18. After day 18, 1 ml of culture was sampled but no BG11 medium was added back into the culture. The experiments were conducted in duplicates.

Product Quantification.

Standard solutions of 3HB were prepared in water using (±)-3-Hydroxybutyric acid sodium salt. Samples of the culture medium were centrifuged at 17,000 xg for 2 min at room temperature and the supernatant was collected for analysis of products on an 1100 series HPLC equipped with a refractive index detector (Agilent, Santa Clara, Calif.). Separation of metabolites was achieved using an Aminex HPX-87H anion-exchange column (Bio Rad Laboratories, Hercules, Calif.). The mobile phase consisted of 5 mM $H_2SO_4$ at an initial flow rate of 0.55 ml/min before immediately and linearly increasing to a final flow rate of 0.8 ml/min over 12 min, followed by an 8 min hold. The column temperature was maintained at 35° C. throughout.

3HB is the precursor for synthesizing the biodegradable plastics poly-3-hydroxybutyrate (PHB), as well as many chiral fine chemicals. For the first two steps in the constructed pathways, namely thiolase and 3-hydroxybutyryl-CoA dehydrogenase, gene pairs from three different bacterial sources were comparatively examined: native *Synechocystis* slr1993 (phaA2) and slr1994 (phaB2) for (R)-3HB, phaA and phaB from *Ralstonia eutropha* H16 for (R)-3HB, and thiI and hbd from *Clostridium acetobutylicum* ATCC824 for (S)-3HB. The final step of all pathways consisted of thioesterase II (encoded by tesB) from *Escherichia coli*. To facilitate carbon flux towards 3HB, slr1829 and slr1830 (encoding PHB polymerase) were deleted from *Synechocystis* to eliminate PHB production.

Construction of 3HB-Producing Strains.

A series of strains were constructed to systematically explore the photosynthetic production of (S)- and (R)-3HB by engineered *Synechocystis* (Table 1) using standard molecular biology protocols. The general strategy is presented in FIG. 1. The *E. coli* thioesterase II encoded by tesB gene has been utilized in each scheme to directly hydrolyze (S)- or (R)-3-hydroxybutyryl-CoA to generate (S)- or (R)-3HB, respectively. We first introduced the tesB gene from *E. coli* into the genome of *Synechocystis* 6803 to construct strain TESB which was expected to realize the conversion of (R)- or (S)-3-hydroxybutyryl-CoA to corresponding 3-HB. To complete the 3HB biosynthesis pathways, we next introduced three different sets of operons into *Synechocystis* TESB to express both thiolase and 3-hydroxybutyryl-CoA dehydrogenase. The resultant strains included HB5 and TAB1, which respectively harbored thiI and hbd from *C. acetobutylicum* ATCC 824 or phaA and phaB from *Ralstonia eutropha* H16. A third strain TPU3 was constructed by placing a Ptac promoter just upstream of the native slr1993 (phaA2)-slr1994 (phaB2) operon to enhance its expression (FIG. 1).

Figure 2:
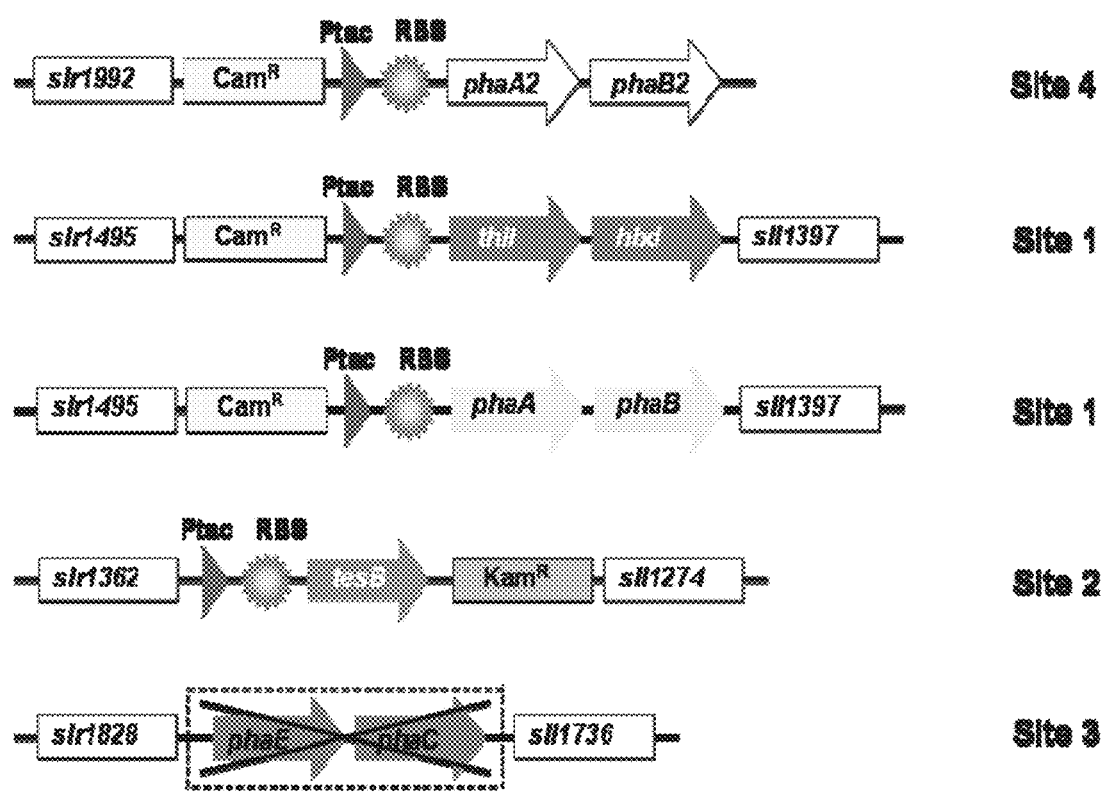
FIG. 2 is a schematic representation of the modification of *Synechocystis* chromosome for 3HB production. Site 1, the site on the genome of *Synechocystis* 6803 between slr1495 and sll1397; Site 2, the site between slr1362 and sll1274; Site 3, the site between slr1828 and sll1736 for phaEC deletion; Site 4, the site between slr1992 and phaA2 (slr1993).

The Ptac promoter has been reported as a strong promoter in *Synechococcus* and *Synechocystis* and was used to initiate high-level expression of isobutanol biosynthetic genes in *Synechococcus*. Here, the Ptac promoter was used to express all of the 3HB pathway genes (FIG. 2). All foreign genes were integrated into the neutral sites of the *Synechocystis* genome where no effect was expected (FIG. 2). Additionally, because native PHB synthesis would compete with 3HB biosynthesis for the intermediate (R)-3-hydroxybutyryl-CoA (FIG. 1), the native operon harboring phaE (slr1829) and phaC (slr1830) which encodes for the PHB polymerase was deleted from the *Synechocystis* genome (through an intermediate strain *Synechocystis* SPA; Table 1) to obtain *Synechocystis* SPA:ΔphaEC strain. Next, three sets of 3HB pathway genes were each introduced into this PHB polymerase-deletion strain in the same way as described above, resulting in *Synechocystis* TESBd, HBd, TABd and TPUd. The genotypic purity of each strain was confirmed by colony PCR in all cases.

Expression of 3HB Biosynthetic Genes in *Synechocystis*.

The 16S rRNA of both wild-type and engineered *Synechocystis* strains was used as the reference to calculate the $\Delta C_T$ values for individual genes when performing the RT-qPCR analysis. RT-qPCR analysis showed that all target genes were successfully transcribed in all engineered strains, and that no detectable phaE or phaC expression was observed in any of the ΔphaEC strains (i.e., TESBd, TPUd, HBd, TABd) (Table 2). In addition, by introducing a Ptac promoter upstream of the native phaA2-phaB2 operon, expression of phaA2 and phaB2 was enhanced in TPU3 by nearly 6- and 120-fold, respectively. Similarly, expression of phaA2 and phaB2 was enhanced by about 4- and 90-fold, respectively, in strain TPUd through the addition of Ptac.

Thus, it was found that the Ptac promoter could be used to effectively transcribe all 3HB pathway genes in *Synechocystis* 6803 and its derivatives. Enzyme activity assay results (Table 3) revealed that thiolase activities of the enhanced-expressed native PhaA2 and *R. eutropha* PhaA were 1.14±0.14 U (μmol/min/ml cell extract) and 13.12±3.36 U, respectively. It is notable that the thiolase activity of PhaA was about 12-fold higher than that of PhaA2. In contrast, no thiolase activity was detected for the *C. acetobutylicum* ThiI. (R)-3-hydroxybutyryl-CoA dehydrogenase activity was detected for PhaB with a value of 0.23±0.15 U, but not for enhanced-expressed PhaB2. (S)-3-hydroxybutyryl-CoA dehydrogenase activity was negative in cell extract of strain HB5 (data not shown). The thioesterase activity reached a value of 0.484±0.044 U using decanoyl-CoA as substrate but 6-fold lower, 0.084±0.021 U, when using butyryl-CoA as substrate (Table 4), which was consistent with the report that TesB biases medium- and long-chain fatty acyl-CoA substrates.

Production of 3HB by the Engineered Cyanobacteria.

Figure 3:
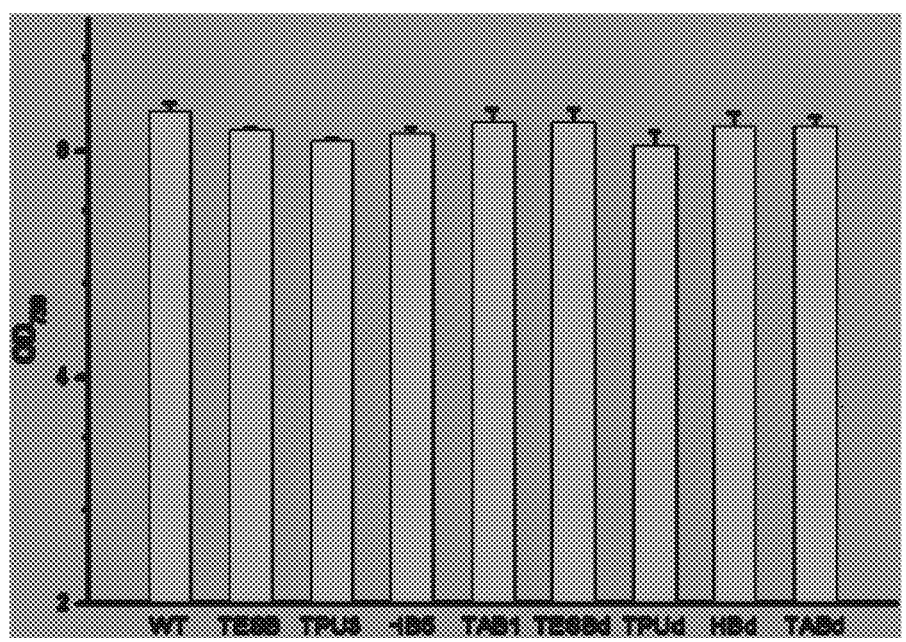
FIG. 3 depicts the cell density of different *Synechocystis* strains cultivated in shaking flasks.
Figure 4:
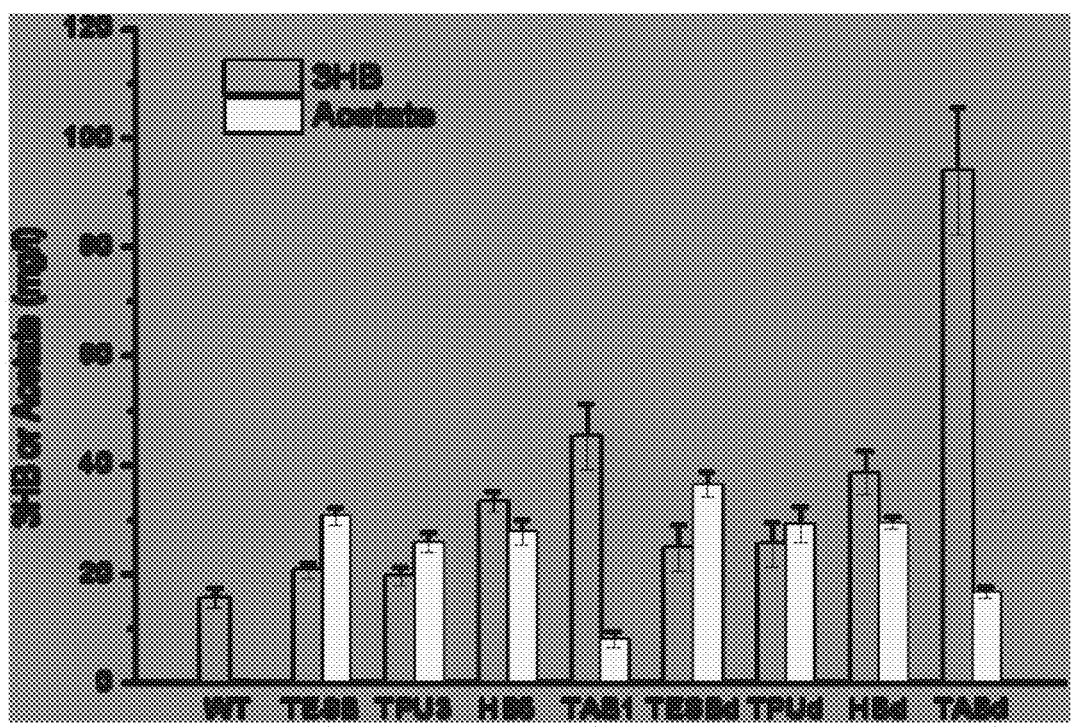
FIG. 4 depicts extracellular production of 3HB by *Synechocystis* 6803 and engineered derivatives. 3HB titers were symbolized as grey bars and acetate titers were symbolized as yellow bars.

After wild-type *Synechocystis* and eight engineered strains were grown photosynthetically for five days, they all reached similar $OD_{730}$ of 8.5-9.0 (FIG. 3). The culture broth was then sampled for HPLC analysis. Under the examined growth conditions, wild-type *Synechocystis* generated and secreted into the culture medium up to 15.5 mg/l 3HB. The introduction and expression of tesB alone in *Synechocystis* (strain TESB) led to a final 3HB titer of about 20.6 mg/l. Interestingly, strain TPU3 in which tesB as well as the native phaA2 and phaB2 were over-expressed with the use of the Ptac promoter, achieved no detectable increase of 3HB production compared to that of strain TESB. Co-expression of tesB with thiI and hbd of *C. acetobutylicum* (strain HB5) resulted in 33.2 mg/l 3HB production. Production of 3HB was boosted to 45.1 mg/l in the culture medium of strain TAB1 which co-expressed tesB with phaA and phaB of *R. eutropha*. Deletion of phaE and phaC further improved 3HB production, as indicated by the ability of strain TABd to reach final titers of about 100 mg/l, nearly 6.5-fold higher than that of the wild-type (FIG. 4).

Notably, expression of *E. coli* tesB also resulted in a dramatic increase of acetate production by our engineered *Synechocystis* relative to the wild-type (FIG. 4), consistent with the previous report about the tesB-over-expressed recombinant *E. coli*. Further experimental results indicated that TesB can catalyze the hydrolysis of acetyl-CoA to acetate with a 33-fold lower activity than that in hydrolysis of butyryl-CoA (Table 5). Nevertheless, with expression of the *R. eutropha* phaA and phaB in strains TAB1 and TABd (Table 1), the acetate production was significantly reduced (FIG. 4). This is probably due to relatively high activities of PhaA and PhaB which drove an increasing portion of acetyl-CoA to form (R)-3-hydroxybutyryl-CoA (FIG. 1); the latter in turn outcompeted acetyl-CoA as substrate for hydrolysis (by TesB), resulting in increase of 3HB production and decrease of acetate biosynthesis.

Improving 3HB Production by Nutrient Supplementation.

Figure 5A:
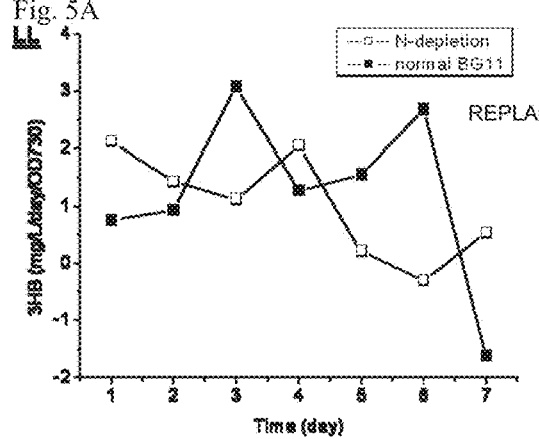
FIGS. 5A-C depict 3HB productivity for unit density of *Synechocystis* TAB1 cell cultures subjected to nitrogen starvation and normal BG11 medium (control) cultures. 3HB production by the normal BG11 medium control dramatically increased by day 3. Culture grown under low light intensity (LL, ~45 $\mu E/m^2/s$), middle light intensity (ML, ~60 $\mu E/m^2/s$) and high light intensity (HL, ~90 $\mu E/m^2/s$) were studied.
Figure 5B:
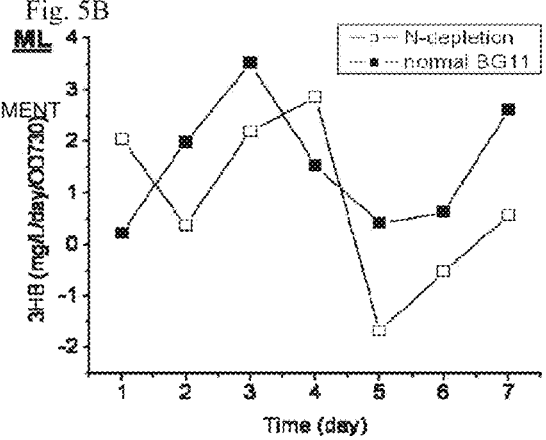
Figure 5C:
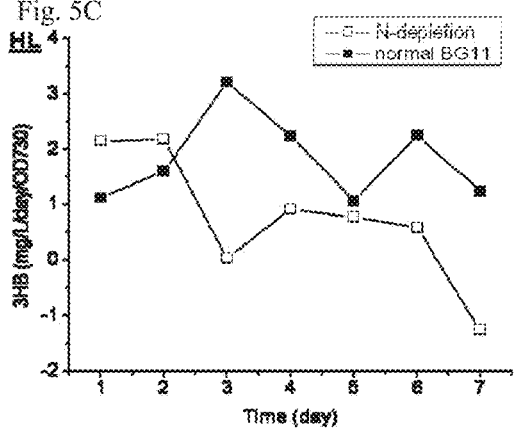
Figure 7:
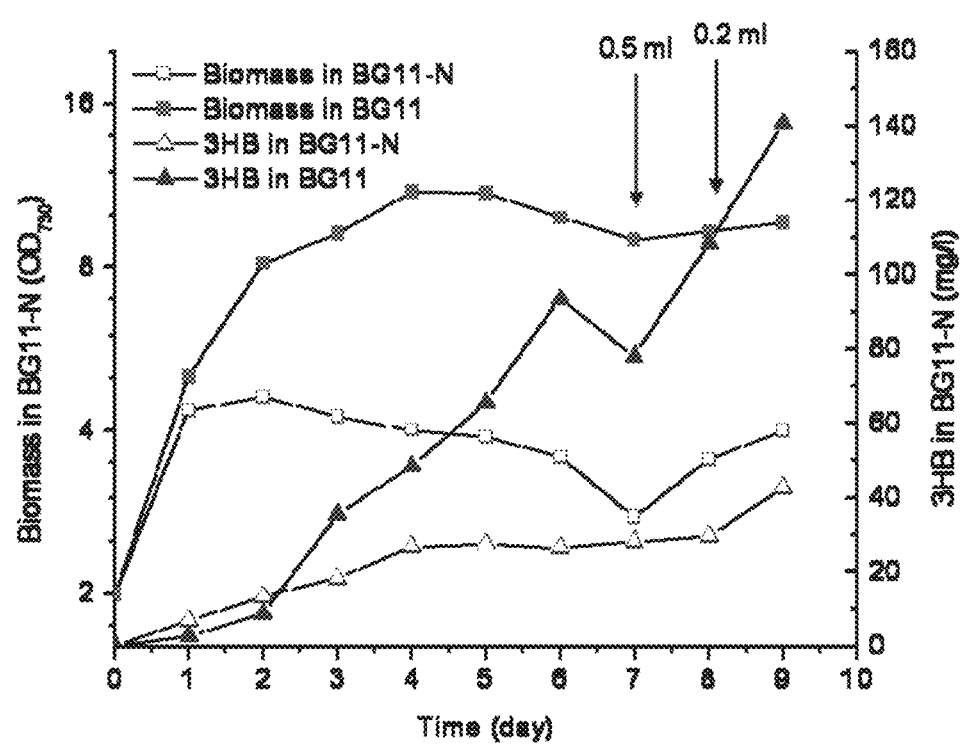
FIG. 7 depicts the effect on 3HB production by nutrient supplementation. When the indicated amount of nutrient was supplemented into the culture after day 7, both biomass and 3HB production started to increase again.

Studies found that nutrient starvation, specifically nitrogen or phosphate depletion, favors PHB accumulation in cyanobacteria. Thus, under these conditions, metabolic flux towards the common pathway intermediate (R)-3-hydroxybutyryl-CoA (3HB pathway & PHB pathway; FIG. 1) should also be increased which might be leveraged to increase 3HB production. We subjected *Synechocystis* TAB1 cells to nitrogen starvation and normal BG11 medium cultures. The results showed that nitrogen-starved cells were able to produce 3HB at higher titers than that of the control (TAB1 grown in BG11) during the first two days. However, 3HB production by the control then dramatically increased from day 3, continuing on through day 6 (FIGS. 5A-C), resulting in overall higher 3HB production than that of the nitrogen-starved counterparts (FIGS. 6A-C). Meanwhile, the cell density of nitrogen-starved culture started a gradual decline after day 2, whereas the cell density of the control kept increasing until day 5 (FIGS. 6A-C). Once a little amount of nutrient was supplemented into the culture after day 7, both biomass and 3HB production started to increase again (FIG. 7).

Figure 8:
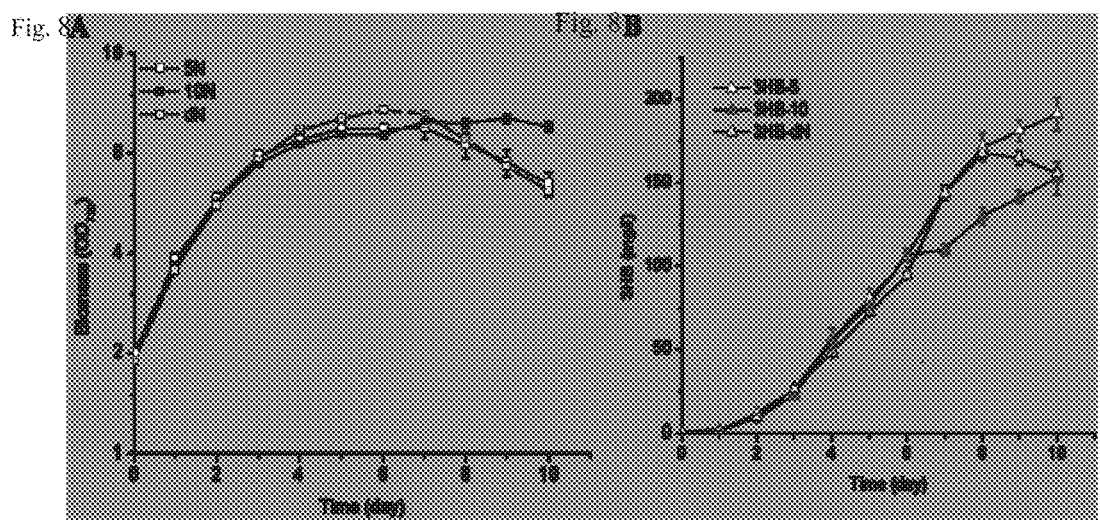
FIGS. 8A-B depict biomass and 3HB production curves of *Synechocystis* strain TABd under different nutrient supplementation conditions. (A) Biomass curves. Grey squares indicate non-N-supplementation; Open squares indicate 5% N-supplementation; solid squares indicate 10% N-supplementation. (B) 3HB production curves. Grey triangles indicate non-N-supplementation; Open triangles indicate 5% N-supplementation; solid triangles indicate 10% N-supplementation.

From the above, it seemed low level of nutrient (herein most importantly nitrate) might positively support both 3HB production and cell viability, which would lead to increased 3HB production. As shown in FIGS. 8A-B, under all nutrient supplementation conditions, strain TABd achieved similar cell densities in about 5 days. The cell density of the non-N and 5%-N supplementation cultures apparently started to decrease after day 7, which could be partially attributed to the daily sampling rather than severe collapse of the cell culture; in contrast, the 10%-N supplementation cultures were apparently able to maintain a relatively stable cell density after day 5.

Figure 9:
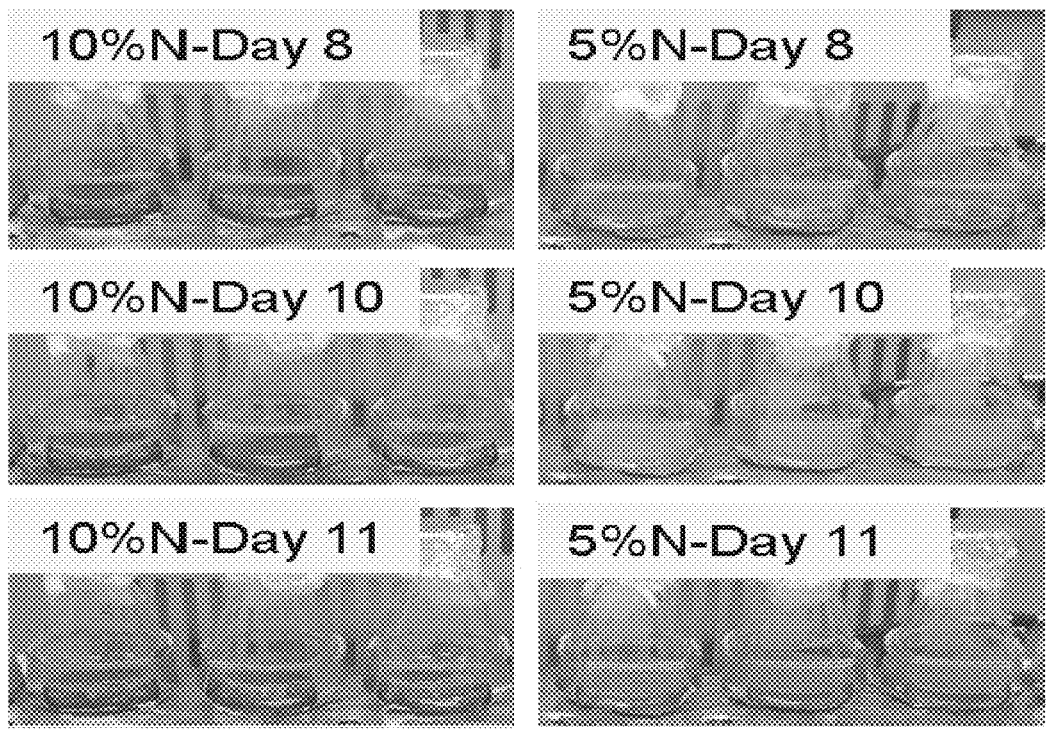
FIG. 9 depicts, after 10 days culture, chlorosis in the non-N and 5%-N (shown) cultures but not in the 10%-N cultures.

Notably, after 10 days culture, chlorosis occurred in the non-N and 5%-N cultures but not in the 10%-N culture (FIG. 9), suggesting pigmented proteins had been degraded in the former cultures. Nevertheless, cells from the yellow non-N and 5%-N cultures still maintained viability as they could turn back to green the next day after being re-suspended in fresh BG11 or BG11-10% N (containing merely 10% of the nitrate relative to BG11) medium, respectively (FIG. 9). Under all three culture conditions, 3HB production firstly underwent a 2-3 days lag phase and then started to increase dramatically. The non-N and 5%-N cultures continued this increase of 3HB titers until day 8 after which 5%-N cultures exhibited a slight increase of 3HB titers while non-N cultures showed a slight decrease of 3HB titers. In contrast, the 10%-N cultures exhibited a much lower 3HB production rate compare to that of 5%-N after day 6. Eventually, The 3HB production achieved titers of 152.7±9.9 mg/l in the 10%-N cultures, 155.9±2.2 mg/l in the non-N cultures and 191.0±10.3 mg/l in the 5%-N cultures (FIGS. 8A-B), indicating that compared to non-N and 10%-N supplementation strategy, 5%-N supplementation is more preferable for 3HB production under the examined culture conditions.

3HB Production from Bicarbonate by Intermittent Medium Exchange.

Figure 10:
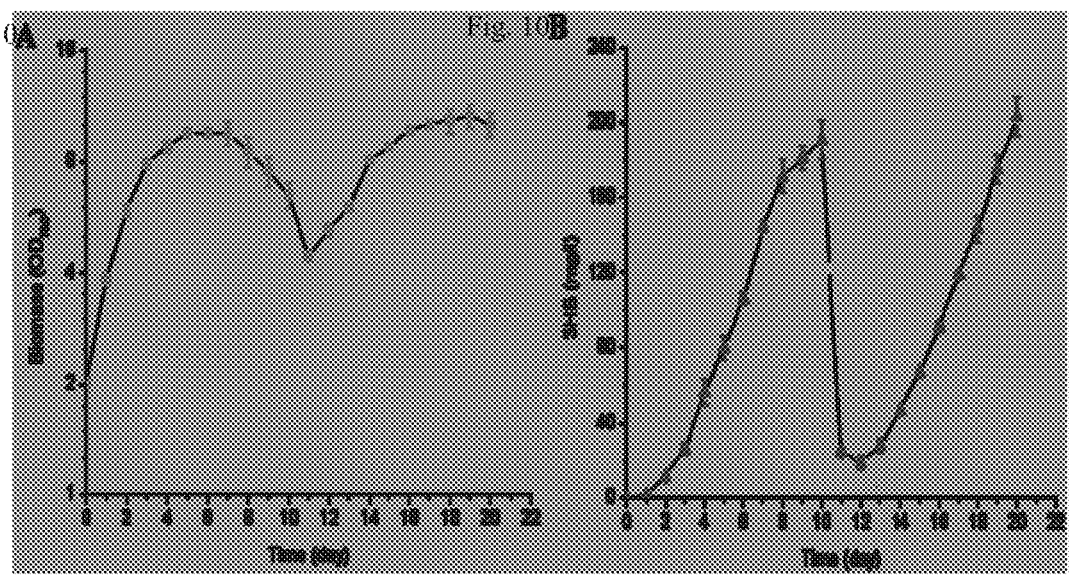
FIGS. 10A-B depict biomass and 3HB production curves of *Synechocystis* strain TABd under 5% N-supplementation condition for 3HB production by medium exchange.

Since 3HB can be secreted out of cells and our engineered *Synechocystis* cells still maintained viability after 10 days cultivation, we next examined the feasibility of applying engineered *Synechocystis* in a continuous production mode where cells from the former 3HB production cycle (Cycle I) can still be used for 3HB production in a latter cycle (Cycle II). We replaced the culture broth with fresh culture medium at the end of each 10-day cultivation cycle for two reasons. First, daily supplementation of $NaHCO_3$ would result in increasing $Na^+$ ion in culture medium which would cause salt stress and therefore impair the cellular activity of cyanobacterial cells. Second, assimilation of $HCO_3^-$ ($4H_2O+4HCO_3^- \rightarrow C_4H_8O_3+4OH^-+9/2O_2$) and $NO_3^-$ ($NO_3^-+3H_2O \rightarrow NH_4^++2OH^-+2O_2$) by *Synechocystis* would alkalize the culture medium and thus also cause stress to cells. As a result, *Synechocystis* TABd exhibited durable and repeatable activity in continuous production of 3HB under our experimental condition. The titers of 3HB in the culture medium could achieve repeatable linear increase after a 2-3 days lag phase at the beginning of each cycle and could finally reach 3HB titers of 191.0±10.3 mg/l (for Cycle I) and 203.3±10.1 mg/l (for Cycle II), respectively (FIGS. 10A-B). Carbonate also is believed to be usable for the carbon source.

3HB Production from Atmospheric $CO_2$.

Figure 11:
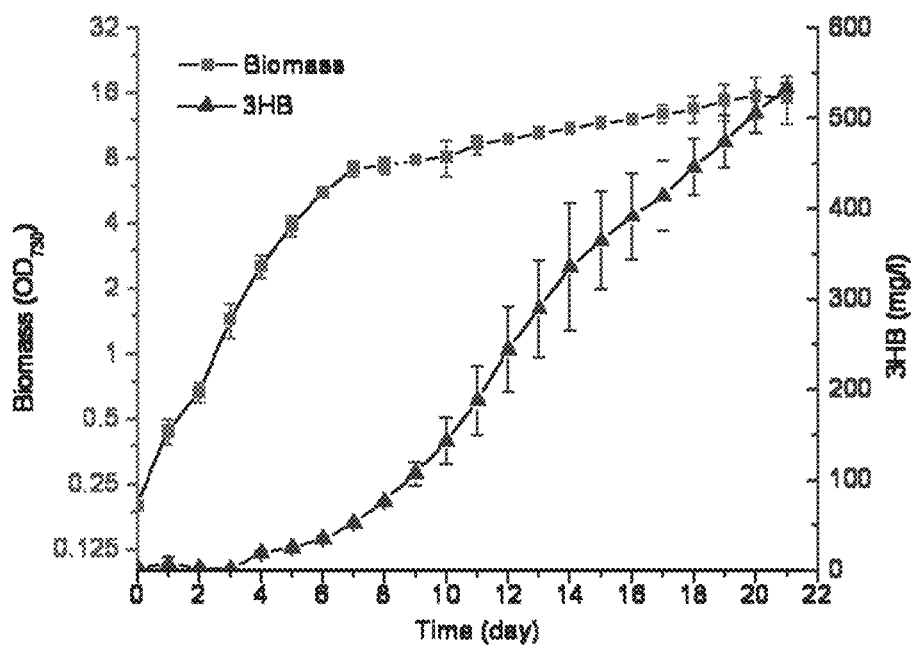
FIG. 11 depicts continuous production of 3HB directly from atmospheric $CO_2$ by *Synechocystis* strain TABd. Solid triangles indicate 3HB titers; solid squares indicate cell densities represented by $OD_{730}$.

The ability of *Synechocystis* strain TABd to photosynthetically produce 3HB using $CO_2$ as sole carbon source was then investigated by continuous aeration of cultures with ambient air. Upon overcoming a lag phase of nearly one week (during which significant biomass growth was observed), 3HB production by *Synechocystis* TABd then quickly accelerated, achieving a titer of 446.5±31.0 mg/l after 18 days of continuous cultivation. At this point, daily BG11 addition into the culture was arrested from days 19 through 21 to probe its effect on continued 3HB production. As can be seen in FIG. 11, 3HB titers continued to increase regardless, and reached a final titer of 533.4±5.5 mg/l by the end of day 21.

It should be noted that at this point, there was no indication that 3HB production would stop; however, we merely elected to stop the experiment. From FIG. 11, it was also observed that starting from day 7, as cell growth declined 3HB production rates were found to dramatically increase (FIG. 7). The relationship here between biomass growth and 3HB production rate is consistent with the results of the former experiments in which $NaHCO_3$ was used as the sole carbon source (FIGS. 8A-B, 6A-C and 7).

The above observations pointed to the possibility of using engineered *Synechocystis* for continuous 3HB production. By following a medium exchange protocol, stable and continuous 3HB production was maintained for a total of 20 days (i.e., two 10-day cycles), resulting in final 3HB titers of ~200 mg/l at the end of each cycle (FIGS. 10A-B). The experiments were stopped after 10 days cultivation due to increasing stresses such as increasing salt concentration and increasing pH in the culture broth. A longer period 3HB production process was developed by using atmospheric $CO_2$ rather than bicarbonate as carbon source, and the results showed that a titer of 533.4±5.5 mg/l 3HB in the culture broth was achieved after 21 days cultivation when cells still kept viability (FIG. 11).

Both of the experiments above demonstrated that by being cultivated and immobilized in a properly controlled photobioreactor system, our engineered *Synechocystis* strains could be employed into a continuous process for 3HB production using only $CO_2$, water and low-cost inorganic compounds as feed stocks and sun light as the energy source. We are expecting that such a carbon-neutral and sustainable process would significantly decrease the manufacture cost in production of 3HB as well as other useful chemicals that can be expanded to.

TABLE 1

Strains and plasmids used in this disclosure

| | Genotype* | Reference |
|---|---|---|
| Strains | | |
| E. coli XL 1-Blue MRF' | Δ(mcrA)183 Δ(mcrCB-hsdSMR-mrr)173 endA1 supE44 thi-1 recA1 gyrA96 relA1 lac [F' proAB lacI$^q$ZΔM15 Tn10 (Tet$^r$)] | Stratagene |
| B. subtilis 168 | | ATCC |
| Synechocystis PCC6803 | Wild-type | ATCC |
| TESB | Ptac-tesB-Kan$^R$ integrated at S2 site in Synechocystis 6803 | This study |
| TPU3 | Ptac-tesB-Kan$^R$ integrated at S2 site and Cm$^R$-Ptac integrated at S4 site | This study |
| HB5 | Ptac-tesB-Kan$^R$ integrated at S2 site and Cm$^R$-Ptac-thil-hbd integrated at S1 site | This study |
| TAB1 | Ptac-tesB-Kan$^R$ integrated at S2 site and Cm$^R$-Ptac-phaA-phaB integrated at S1 site | This study |
| SPA | Ptac-adhe2 integrated at S2 site | Stored in lab |
| SPA:SPSK3 | Ptac-adhe2 integrated at S2 site and Ptac-sacB-Kan$^R$ integrated at S3 site | This study |
| SPA:ΔphaEC | Ptac-adhe2 integrated at S2 site, phaE and phaC deleted at S3 site | This study |
| TESBd | phaE and phaC deleted at S3 site, Ptac-tesB-Kan$^R$ integrated at S2 site | This study |
| TPUd | phaE and phaC deleted at S3 site, Ptac-tesB-Kan$^R$ integrated at S2 site, Cm$^R$-Ptac integrated at S4 site | This study |
| HBd | phaE and phaC deleted at S3 site, Ptac-tesB-Kan$^R$ integrated at S2 site, Cm$^R$-Ptac-thil-hbd integrated at S4 site | This study |
| TABd | phaE and phaC deleted at S3 site, Ptac-tesB-Kan$^R$ integrated at S2 site, Cm$^R$-Ptac-phaA-phaB integrated at S4 site | This study |
| Plasmids | | |
| pBluescript II SK(+) | Amp$^R$, pUC ori, f1(+) ori | Stratagene |
| pACYC184 | Cm$^R$, Tet$^R$, p15A ori | New England BioLabs |
| pET-30a(+) | Kan$^R$, lacI, pBR322 ori, f1 ori | Novagen |
| pETphaAphaB | phaA, phaB integrated between the NcoI and AvrII sites of pETDuet-1 (Amp$^R$, pBR322 ori) | Nielsen's Lab |
| pBS-SRSL | SR12-SL12 inserted between the SacI and KpnI sites of pBluescript II SK(+) | This study |
| pBS-SPT | Ptac-thil inserted between the BamHI and SalI sites of pBS-SRSL | This study |
| pBS-SPTH | hbd integrated between the NcoI and SalI sites of pBS-SPT | This study |
| pBS-SCat | NcoI-removed cat (Cm$^R$) integrated into the PstI and BamHI sites of pBS-SRSL | This study |
| pBS-SCPTH | Ptac-thil-hbd integrated between the NcoI and SalI sites of pBS-SPT | This study |
| pBS-SCPTH2 | MluI site added between thil and hbd of pBS-SCPTH | This study |
| pBS-SCPTB | phaB inserted between the MluI and HindIII sites of pBS-SCPTH2 | This study |
| pBS-SCPAB | Ptac-phaA inserted between the BamHI and MluI sites of pBS-SCPTB | This study |
| pBS-SCG | GTP fragment inserted between the SacI and PstI sites of pBS-SCat | This study |
| pBS-GCPU | Ptac-PHAU inserted between the BamHI and KpnI sites of pBS-SCG | This study |
| pBS-S2 | SR56-SL56 inserted into the SacI and XhoI sites of pBluescript II SK(+) | This study |
| pBS-S2K | kan (Kan$^R$) inserted between MluI and SalI sites of pBS-S2 | This study |
| pBS-SPtTeK | Ptac-tesB integrated between BglII and HindIII site of pBS-S2K | This study |
| pBS-SPTK | PpsaD-thil integrated between the BamHI and MluI sites of pBS-S2K | This study |
| pBS-SPtK | Ptac inserted between the BamHI and NdeI sites of pBS-SPTK | This study |
| pBS-SPSK2 | sacB inserted between the NdeI and MluI sites of the pBS-SPtK | This study |
| pBS-PHA | PHA inserted between the XhoI and SacI sites of pBS-S2 | This study |
| pBS-SPSK3 | Ptac-sacB-kan of pBS-SPSK2 inserted between BamHI and SalI of pBS-PHA | This study |

*S1, the site on the genome of Synechocystis 6803 between slr1495 and sll1397; S2, the site between slr1362 and sll1274; S3, the site between slr1828 and sll1736; S4, the site between slr1992 and phaA2.

TABLE 2

Expression analysis of 3HB pathway genes by RT-qPCR*

| | ΔC$_T$ | | | | | | | |
|---|---|---|---|---|---|---|---|---|
| Gene | WT | TPU3 | HB5 | TAB1 | TESBd | TPUd | HBd | TABd |
| tesB | n.d. | 10.87 ± 0.07 | 10.37 ± 0.22 | 11.19 ± 0.11 | 10.44 ± 0.12 | 12.05 ± 0.24 | 10.83 ± 0.15 | 10.94 ± 0.12 |
| phaA2 | 20.85 ± 0.06 | 18.17 ± 0.16 | — | — | — | 18.75 ± 0.26 | — | — |
| phaA | n.d. | — | — | 12.24 ± 0.01 | — | — | — | 12.04 ± 0.11 |
| thil | n.d. | — | 15.28 ± 0.09 | — | — | — | 15.30 ± 0.46 | — |
| phaB2 | 19.30 ± 1.07 | 12.42 ± 0.28 | — | — | — | 12.84 ± 0.07 | — | — |
| phaB | n.d. | — | — | 12.25 ± 0.26 | — | — | — | 12.50 ± 0.05 |
| hbd | n.d. | — | 17.14 ± 0.26 | — | — | — | 17.62 ± 0.01 | — |

TABLE 2-continued

Expression analysis of 3HB pathway genes by RT-qPCR*

| Gene | ΔC$_T$ | | | | | | | |
|------|--------|------|-----|------|--------|------|------|------|
|      | WT     | TPU3 | HB5 | TAB1 | TESBd  | TPUd | HBd  | TABd |
| phaE | 15.52 ± 0.28 | — | — | 15.76 ± 0.26 | n.d. | n.d. | n.d. | n.d. |
| phaC | 17.17 ± 0.48 | — | — | 17.20 ± 0.30 | n.d. | n.d. | n.d. | n.d. |

*"n.d.", "not detectable". "—", experimental data was not available. The relative abundance of different mRNA molecules could be estimated using $2^{-\Delta C_T}$; the bigger the $\Delta C_T$ value, the lower abundance of the corresponding mRNA is.

TABLE 3

Enzyme activities for engineered strains.

| Enzyme (gene) | Activities* | Examined strain | Strains with same expression cassette |
|---|---|---|---|
| Thiolase (phaA2) | 1.14 ± 0.14 | TPU3 | TPUd |
| Thiolase (thl) | n.d. | HB5 | HBd |
| Thiolase (phaA) | 13.12 ± 3.36 | TAB1 | TABd |
| (R)-3-Hydroxybutyryl-CoA dehydrogenase (phaB2) | n.d. | TPU3 | TPUd |
| (S)-3-Hydroxybutyryl-CoA dehydrogenase (hbd) | n.d. | HB5 | HBd |
| (R)-3-Hydroxybutyryl-CoA dehydrogenase (phaB) | 0.23 ± 0.15 | TAB1 | TABd |
| Thioesterase (tesB) | 0.084 ± 0.021 | TESB | TPU3, HB5, TAB1, TESBd, TPUd, HBd, TABd |

*Enzyme activities were given in μmol/min/mL cell extract;
"n.d." stands for "not detectable".
"—" means experimental data was not available.

TABLE 4

| Substrate | Thioesterase (TesB) activities* | Examined strain |
|---|---|---|
| Decanoyl-CoA | 0.484 ± 0.044 | Synechocystis strain TESB |
| Butyryl-CoA | 0.084 ± 0.021 | Synechocystis strain TESB |
| Acetyl-CoA | n.d. | Synechocystis strain TESB |

TABLE 5

| Substrate | Thioesterase (TesB) activities* | Examined strain |
|---|---|---|
| Butyryl-CoA | 10.451 ± 1.924 | E. coli XL1-Blue/pBS-SPtTeK |
| Acetyl-CoA | 0.319 ± 0.022 | E. coli XL1-Blue/pBS-SPtTeK |
| Butyryl-CoA | n.d. | E. coli XL1-Blue/pBS-S2K |
| Acetyl-CoA | n.d. | E. coli XL1-Blue/pBS-S2K |

*Enzyme activities were given in μmol/min/mL cell extract;
"n.d." stands for "not detectable".

TABLE 6

Strains and plasmids used in this paper.

| Strains | Genotype* | References |
|---|---|---|
| E. coli XL1-Blue MRF' | Δ(mcrA)183 Δ(mcrCB-hsdSMR-mrr)173 endA1 supE44 thi-1 recA1 gyrA96 relA1 lac [F' proAB lacI$^q$ZΔM15 Tn10 (Tet$^r$)] | Stratagene |
| Synechocystis ABd | P$_{tac}$-adhe2 integrated at S2 site, phaE and phaC deleted at S3 site, Cm$^R$-P$_{tac}$-phaA-phaB1 integrated at S1 site | This study |
| TTrK | P$_{tac}$-tesB-T1-Kan$^R$ integrated at S2 site, Cm$^R$-P$_{tac}$-phaA-phaB1 integrated at S1 site, phaE and phaC deleted at S3 site | This study |
| SD-TrK | P$_{tac}$-SD-tesB-T1-Kan$^R$ integrated at S2 site, Cm$^R$-P$_{tac}$-phaA-phaB1 integrated at S1 site, phaE and phaC deleted at S3 site | This study |
| UTR-TrK | P$_{tac}$-UTR-tesB-T1-Kan$^R$ integrated at S2 site, Cm$^R$-P$_{tac}$-phaA-phaB1 integrated at S1 site, phaE and phaC deleted at S3 site | This study |
| PTrK12 | P$_{psbA12}$-tesB-T1-Kan$^R$ integrated at S2 site, Cm$^R$-P$_{tac}$-phaA-phaB1 integrated at S1 site, phaE and phaC deleted at S3 site | This study |
| PTrK14 | P$_{psbA14}$-tesB-T1-Kan$^R$ integrated at S2 site, Cm$^R$-P$_{tac}$-phaA-phaB1 integrated at S1 site, phaE and phaC deleted at S3 site | This study |
| PTrK16 | P$_{psbA12}$-P$_{tac}$-tesB-T1-Kan$^R$ integrated at S2 site, Cm$^R$-P$_{tac}$-phaA-phaB1 integrated at S1 site, phaE and phaC deleted at S3 site | This study |
| SPA:ΔphaEC | P$_{tac}$-adhe2 integrated at S2 site, phaE and phaC deleted at S3 site | This study |
| ABd-SPSK2 | P$_{tac}$-sacB-kan integrated at S2 site, phaE and phaC deleted at S3 site, Cm$^R$-P$_{tac}$-phaA-phaB1 integrated at S1 site | This study |
| ABd-TTe | Ptac-tesB integrated at S2 site, phaE and phaC deleted at S3 site, Cm$^R$-P$_{tac}$-phaA-phaB1 integrated at S1 site | This study |
| TTB2K3 | phaE and phaC deleted at S3 site, P$_{tac}$-tesB integrated at S2 site, P$_{tac}$-tesB$_{opt}$-phaB2$_{eu-opt}$-kan integrated at S3 site, Cm$^R$-P$_{tac}$-phaA-phaB1 integrated at S1 site | This study |

TABLE 6-continued

Strains and plasmids used in this paper.

| Strains | Genotype* | References |
|---|---|---|
| ABdTB | phaE and phaC deleted at S3 site, $P_{tac}$-tesB$_{opt}$-phaB2$_{eu\text{-}opt}$ integrated at S3 site, Cm$^R$-$P_{tac}$-phaA-phaB1 integrated at S1 site | This study |
| PTrK16-Int | $P_{psbA12}$-$P_{tac}$-tesB-T1-Kan$^R$ integrated at S2 site, phaE and phaC deleted at S3 site | This study |
| R154 | $P_{psbA12}$-$P_{tac}$-tesB-T1-Kan$^R$ integrated at S2 site, phaE and phaC deleted at S3 site, Cm$^R$-$P_{tac}$-phaA-(RBS$_{opt}$)-phaB1 integrated at S1 site | This study |
| R168 | $P_{psbA12}$-$P_{tac}$-tesB-T1-Kan$^R$ integrated at S2 site, phaE and phaC deleted at S3 site, Cm$^R$-$P_{psbA12}$-$P_{tac}$-phaA-(RBS$_{opt}$)-phaB1 integrated at S1 site | This study |

*S1, the site on the genome of Synechocystis 6803 between slr1495 and sll1397; S2, the site between slr1362 and sll1274; S3, the site between slr1828 and sll1736.

TABLE 7

Enzyme activity assay for engineered Synechocystis strains*.

| Strain | Genotype | Acetoacetyl-CoA reductase | Thioesterase |
|---|---|---|---|
| TTrK | $P_{tac}$-tesB, $P_{tac}$-phaA-phaB1, ΔphaEC | 0.063 ± 0.013 | 0.345 ± 0.010 |
| PTrK16 | $P_{psbA12}$-$P_{tac}$-tesB, $P_{tac}$-phaA-phaB1, ΔphaEC | 0.078 ± 0.033 | 0.243 ± 0.014 |
| TTB2K3 | $P_{tac}$-tesB, $P_{tac}$-phaA-phaB1, $P_{tac}$-tesB$_{opt}$-phaB2$_{eu\text{-}opt}$, ΔphaEC | 0.093 ± 0.007 | 0.386 ± 0.010 |
| ABdTB | $P_{tac}$-phaA-phaB1, $P_{tac}$-tesB$_{opt}$-phaB2$_{eu\text{-}opt}$, ΔphaEC | n.a. | 0.161 ± 0.014 |
| R154 | $P_{tac}$-tesB, $P_{tac}$-phaA-(RBS$_{opt}$)-phaB1, ΔphaEC | 0.139 ± 0.020 | n.a. |

*The cells for enzyme assay were collected after growing in BG11 (10 mM TES-NaOH, pH 8.0) for 12 hours under an irradiation of 60 μE/m$^2$/s.

Further Examples

Materials and Methods
Culture Conditions

All recombinant plasmids were constructed and stored using E. coli XL1-Blue MRF' (Stratagene, La Jolla, Calif.) as the host strain. Synechocystis strains were grown in BG11 medium (Rippka et al., 1979) supplemented with 50 mM NaHCO$_3$ under a light intensity of 60 μE/m$^2$/s unless otherwise specified. For BG11-agar plates, 10 mM TES (pH 8.0), 3 g/L thiosulfate and 1.5% agar was supplemented into BG11 medium before autoclaving.

Modification of Synechocystis Genome

The chromosome of Synechocystis 6803 was modified using the same methods as described previously (Wang et al., 2013). The genotype of each engineered Synechocystis strain is described in Table 6. The genotypic purity of each strain was achieved by a series of streaking of the colonies on the antibiotic-supplemented BG11 plates and was confirmed by colony PCR.

Production of (R)-3HB from Bicarbonate

Synechocystis strains were inoculated in 50 ml flasks containing 10 ml BG11 (10 mM TES-NaOH) to an initial OD$_{730}$ of 2.0. Then, cells were incubated in a shaking bed (150 rpm) at 30° C. with a light intensity of 60 μE/m$^2$/s except otherwise specified. Every day, 0.05 ml cell culture was sampled for analysis of the OD$_{730}$ before 0.5 ml 1.0M NaHCO$_3$ was added to each culture and the pH was adjusted to ~8.0 by 10 N HCl. Each cell culture was sampled at the end of day 3 and day 5, respectively, for analysis of the (R)-3HB titers. All culture experiments were conducted at least in triplicate for each strain.

Production of 3HB from Carbon Dioxide

Synechocystis was inoculated into a 125 ml flask containing 50 ml autoclaved BG11 (10 mM TES-NaOH) medium to an initial OD$_{730}$ of 0.2. The culture was placed at 30° C. with continuous illumination of 100 μE/m$^2$/s, bubbled with ambient air during the first 24 h and then switched to 1% (v/v) CO$_2$. The aeration rate was set as 37.5 mL/min. Every day, 1 mL of culture was sampled and 1.25 mL 2-fold concentrated sterilized BG11 medium was added back into the culture until day 21. The experiments were conducted in duplicates.

Gene Expression Analysis by RT-qPCR

Cells were resuspended to an initial OD$_{730}$ of 2.0 before they were grown in BG11 (10 mM TES-NaOH) medium under continuous illumination of 60 μE/m$^2$/s. Daily, 0.05 mL cell culture was sampled for analysis of the OD$_{730}$ before 0.5 mL 1.0M NaHCO$_3$ was added to each culture and the pH was adjusted to ~8.0 by 10 N HCl. At 3.5 days of cultivation, approximately 1.67×10$^8$ Synechocystis cells (assuming OD$_{730}$ of 0.6 equals to 10$^8$ cells/ml; Liu et al., 2011) were collected by centrifugation at 17,000 g, 4° C. for 1 min. The supernatant was discarded and the cell pellet was used for RNA extraction using ZR Fungal/Bacterial RNA Mini-Prep™ Kit (ZYMO Research, Irvine, Calif.). The RNA was then quantified by RT-qPCR using methods described previously (Gao et al., 2011). The primers used for RT-qPCR analysis is listed in Supplementary Data.

Enzyme Activity Assay

Synechocystis cells were grown as described above for 12 hours. At the end of the cultivation, approximately 1.67×10$^9$ Synechocystis cells were collected by centrifugation at 8000 g, 4° C. for 5 min. The supernatant was discarded and the cell pellets were frozen on dry ice and stored at −80° C. before the assay. For the thioesterase enzyme activity assay, the cell pellet was resuspended with 500 μL ice-cold 0.1 M Tris-HCl (pH 7.5) and lysed by sonication (100 cycles of 3-s-on/3-s-off) in ice bath. The cell lysate was centrifuged at 17000 g, 4° C. for 10 min before the supernatant was analyzed for the thioesterase activity following the previous protocols but using Butyryl-CoA as the substrate (Wang et al., 2013). For the acetoacetyl-CoA reductase enzyme activity assay, the cell pellet was resuspended in 500 μL ice-cold Buffer A [50 mM K$_2$HPO$_4$—HCl (pH 7.5), 10% glycerol, 1 mM EDTA, 1 mM DTT] with 0.1 mM PMSF and lysed by sonication (20 cycles of 3-s-on/3-s-off) in ice bath. The supernatant was analyzed for the acetoacetyl-CoA reductase activity using the protocol established previously (Wang et al., 2013).

Product Quantification

The (R)-3HB and acetate concentrations were quantified by an 1100 series HPLC using the method described previously (Wang et al., 2013). Briefly, samples of the *Synechocystis* culture were centrifuged at 17,000 g for 1~2 min at room temperature and the supernatant was properly diluted before being analyzed on HPLC equipped with an Aminex HPX-87H anion-exchange column (Bio-Rad Laboratories, Hercules, Calif.) and a refractive index detector (Agilent, Santa Clara, Calif.). The column temperature was maintained at 35° C. during operation. The mobile phase was 5 mM $H_2SO_4$ and the flow rate was set as a linear gradient from 0.55 ml/min to 0.8 ml/min over 12 min, followed by an 8 min hold (Tseng et al., 2009).

Results and Discussion

Construction of a Promoter Library

Figure 13:
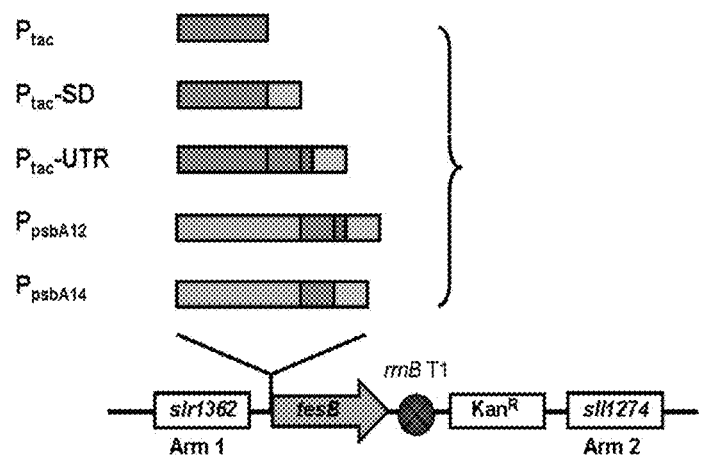
FIG. 13 is a schematic structure of the five promoters.

Since promoter is the key element to initiate the expression of the interest genes, to screen out a strong promoter is critical to improving the gene expression level in the host strain. Herein, a promoter library was constructed for screening promoters with desirable performance. The library included the constitutive $P_{tac}$ promoter, the wild type light-inducible $P_{psbA2}$ promoter from *Synechocystis* 6803, and three derivative promoters (FIG. 13). *Synechocystis* strain TTrK, with all the 3HB biosynthesis genes expressed via the Ptac promoter, was reconstructed from the TABd strain (Wang et al., 2013) by placing an additional rrnB T1 terminator downstream the tesB gene (Table 6). The $P_{tac}$ promoter upstream the tesB gene was replaced by the wild type psbA2 promoter (thereafter $P_{psbA12}$), resulting in strain PTrK12. It was reported that the 5'-untranslated region (UTR) of the $P_{psbA12}$ promoter from *Synechocystis* 6803 plays an important role in stabilizing the psbA2 mRNA (Sakurai et al., 2012). It was therefore assumed that the 5'-UTR of $P_{psbA12}$ promoter might be placed upstream of the interest gene to increase the mRNA stability of the corresponding downstream gene(s). To this end, the whole 5'-UTR or merely the ribosome binding site (RBS, including the SD sequence) of the psbA2 gene was placed downstream of the $P_{tac}$ promoter, resulting in promoters $P_{tac}$-UTR or $P_{tac}$-SD, respectively (FIG. 13). In addition, since the AU-box in the 5'-UTR of $P_{psbA2}$ was suggested to be a negative element for gene expression (Agrawal et al., 2001; Sakurai et al., 2012), the AU-box has been deleted from the $P_{psbA12}$ promoter to form promoter $P_{psbA14}$ (FIG. 13).

The Performance of Promoters

Figure 14A:
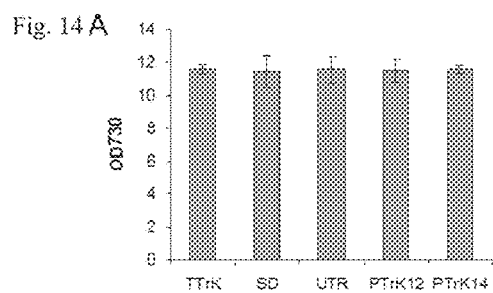
FIGS. 14A-D are characterizations of the five promoters. (A) Cell density of strains expressing tesB using each promoter. (B) Production of (R)-3HB by each strain. (C) tesB mRNA abundance in each engineered strain. (D) Acetate accumulation in the culture medium of each engineered strain.
Figure 14B:
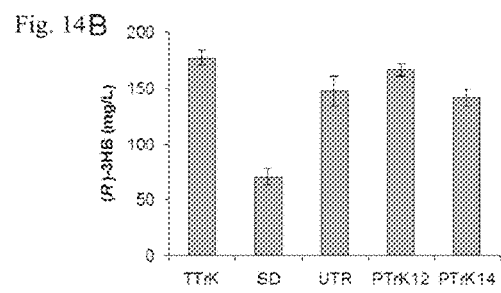

Since activities of the thioesterase (encoded by tesB) and the acetoacetyl-CoA reductase (encoded by phaB1) were identified as the possible bottlenecks for (R)-3HB biosynthesis in *Synechocystis* based on the enzyme activity assay results (Wang et al., 2013, 2014), the performance of the above five promoters were characterized through expressing the tesB gene in the phaA-phaB-expressing strains (Table 6). When the engineered strains were grown under photoautotrophic conditions, no significant difference was observed among the strains regarding the cell growth rates (FIG. 14A-D). However, the 3HB production titers exhibited considerable variability among the five strains (FIG. 14B). Strain TTrK (Pac) exhibited the highest 3HB productivity, reaching 176.9±6.4 mg/L in five days. Strain PTrK12 ($P_{psbA12}$) produced 166.1±5.2 mg/L of 3HB, slightly lower than that of strain TTrK ($P_{tac}$). The 3HB productivities of strains UTR-TrK ($P_{tac}$-UTR) and PTrK14 ($P_{psbA14}$) were slightly lower than that of strain PTrK12 ($P_{psbA12}$), reaching 147.5±13.3 mg/L and 141.3±7.3 mg/L, respectively. Strain SD-TrK ($P_{tac}$-SD) produced the least amount of 3HB, reaching only 70.2±7.0 mg/L, less than half of that of any other strain (FIG. 14B).

Figure 14C:
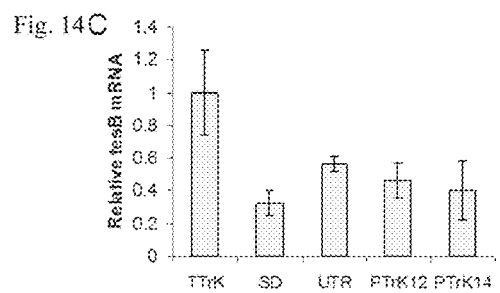

RNA analysis of the above five strains indicated that the mRNA level of gene tesB in strain TTrK was the highest among all investigated strains (FIG. 14C) which is consistent with its highest 3HB productivity (FIG. 14B), suggesting that the $P_{tac}$ promoter might be the strongest promoter under the examined culture condition. In contrast, the tesB mRNA level in strain SD-TrK was the lowest (FIG. 14C). Since modification of the 5'-UTR was assumed to have little impact on the gene transcription, our finding indicated that the apparent lower abundance of the tesB mRNA in SD-TrK was attributed to the poorer stability of the mRNA product that contained the RBS region of the $P_{psbA12}$ promoter. This result was consistent with the previous report that the RBS of the $P_{psbA12}$ promoter was a target of the RNase E/G in *Synechocystis* 6803 (Horie et al., 2007; Sakurai et al., 2012). Interestingly, the tesB mRNA abundance was 57% higher in the strain UTR-TrK compared to that of strain SD-TrK, consistent with the ~2-fold higher 3HB production rate (FIG. 14B). It suggested that the AU-box and the 19-bp upstream sequence (from the $P_{psbA12}$ promoter) in the $P_{tac}$-UTR promoter has a positive impact on expression of the downstream gene. While the AU-box is also a target of the RNase E, this region may be bound by the intrinsic cis-coded as RNA "PsbA2R" and therefore protect the mRNA from degradation by endoribonuclease RNase E/G in *Synechocystis* (Horie et al., 2007; Sakurai et al., 2012). Moreover, after the AU-box was removed, the $P_{psbA14}$ promoter did not show any improved expression of the tesB mRNA (FIG. 14C) and in contrast, the 3HB and acetate production titers slightly decreased compared to those of the strain PTrK12 (FIG. 14B, D).

Figure 14D:
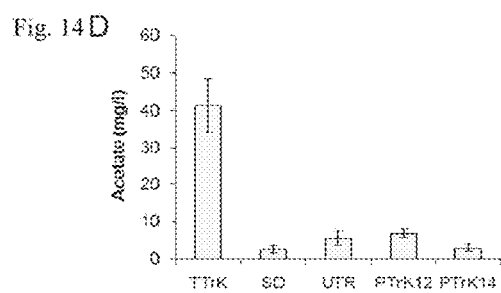

Interestingly, although the tesB expression levels in strains SD-TrK, UTR-TrK, PTrK12 and PTrK14 range from 30% to 60% relevant to that of the strain TTrK (FIG. 14C), the acetate accumulation in these strains reached merely less than 20% of that of strain TTrK (FIG. 14D). TesB has low activity on acetyl-CoA (Wang et al., 2013), and the acetyl-CoA pool in each strain is presumably same as indicated by the same cell growth rate (FIG. 14A). Therefore, the acetate titer may serve as an indicator of the TesB enzyme activity in each strain. The unmatched TesB enzyme activities (FIG. 14C) and mRNA abundance (FIG. 14D) is probably attributed to the different translation efficiency of different promoters, which is discussed thoroughly later on.

Construction and Characterization of a Dual Promoter

Figure 15A:
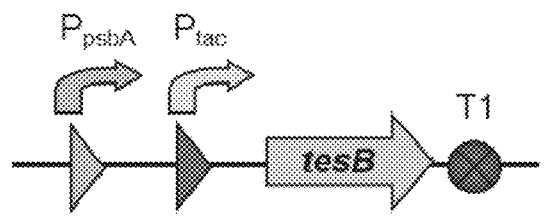
FIGS. 15A-E are characterizations of the dual promoter system in strain PTrK16. (A) Schematic representation of the dual promoter system. (B) Cell densities for strains TTrK and SPTrK16 after growing under a light intensity of 60 $\mu E/m^2/s$ for 5 days. (C) Production of (R)-3HB and acetate by strains TTrK and PTrK16. (D) tesB mRNA relative abundance on day 3.5. (E) Thioesterase activity analysis for TesB.
Figure 15B:
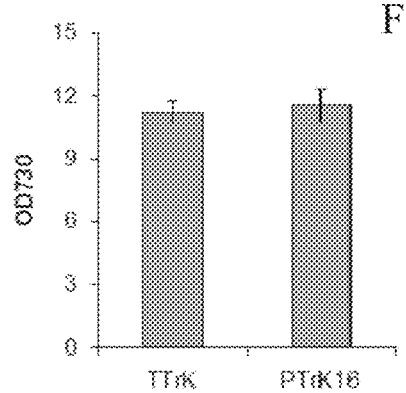
Figure 15C:
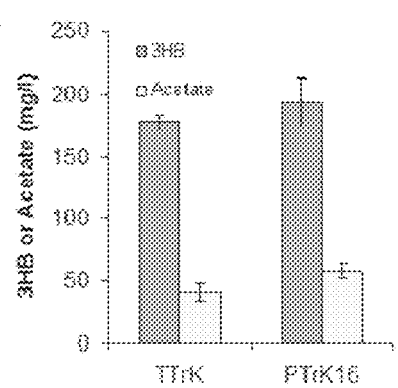

The $P_{tac}$ and the $P_{psbA12}$ promoter were recombined together to form a cascade structure (FIG. 15A) in order to investigate if the expression of the downstream gene can be enhanced in such a way. As a result, there was no significant difference between strains PTrK16 and TTrK regarding to the cell growth rate (FIG. 15C), (R)-3HB production and acetate accumulation (FIG. 15C). RT-qPCR analysis results indicated that the abundance of tesB mRNA in strain PTrK16 and TTrK was at the same level on day 3.5 (FIG. 15D), though the tesB mRNA in strain PTrK16 reached only approximately 70% of that in strain TTrK on day 0.5. The results were further confirmed by the enzyme activity assay (FIG. 15E; Table 7).

Figure 12:
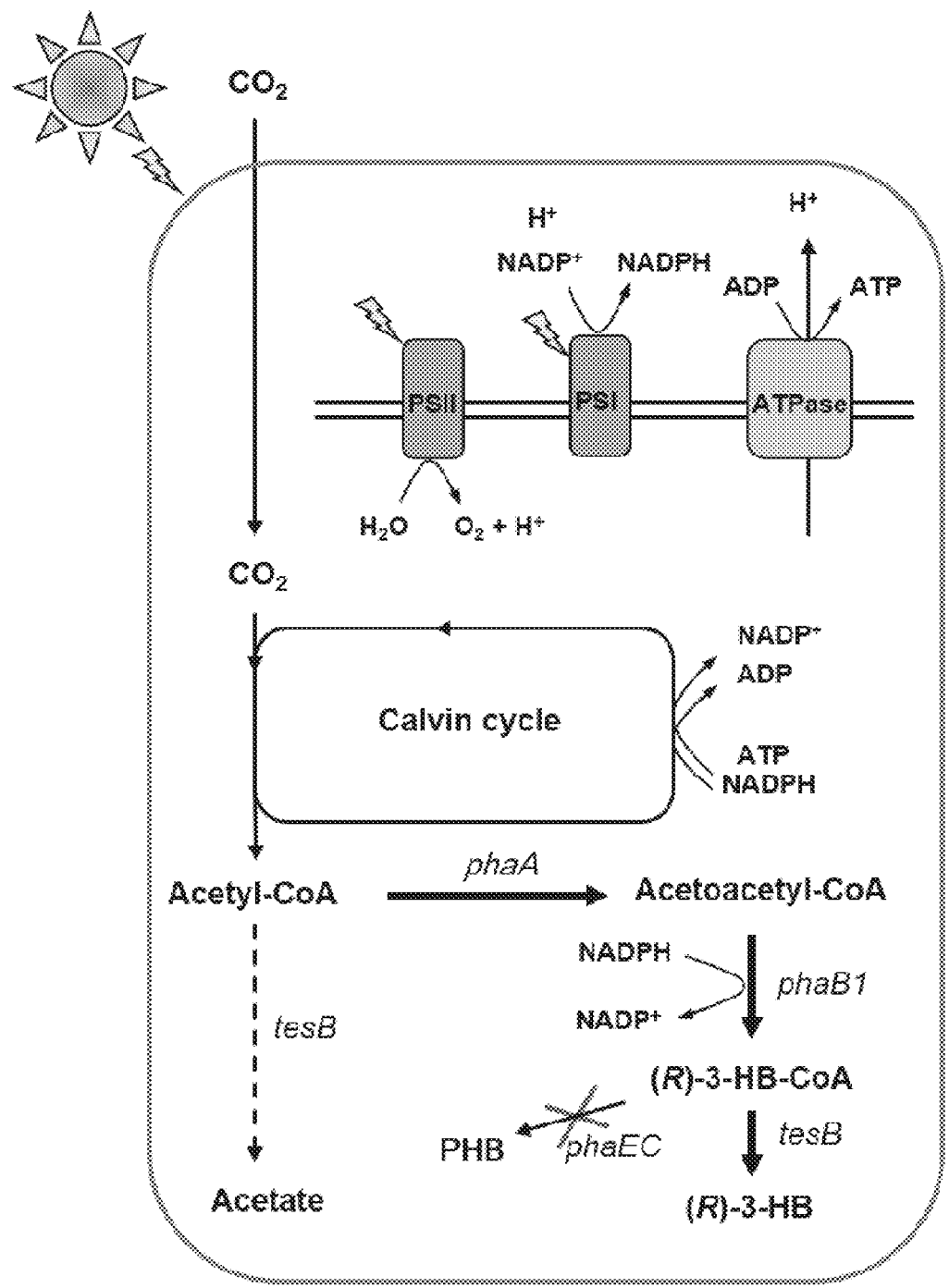
FIG. 12 is a schematic representation of (R)-3HB biosynthesis from $CO_2$ in engineered *Synechocystis*.

Mitigation of the Rate-Limiting Step in (R)-3HB Biosynthesis with Increased Light Intensity Though the tesB mRNA abundance was 2-fold higher (FIG. 14C) and the thioesterase activity (indicated by the acetate titer; FIG. 14D) was more than 5-fold higher in strain TTrK compared to that of strain UTR-TrK, it merely led to marginal increase in production of (R)-3HB in strain TTrK (FIG. 14B). It implied that the metabolic flux between the acetyl-CoA and the (R)-3HB-CoA might be the rate-limiting factor for (R)-3HB biosynthesis (FIG. 12). In other words, the thiolase (PhaA) or the acetoacetyl-CoA reductase (PhaB) activity might be the rate-limiting step for (R)-3HB biosynthesis. Thiolase PhaA catalyzes the condensation of two molecules of acetyl-CoA to produce acetoacetyl-CoA, but this reaction is reversible and it strongly favors the hydrolysis of acetoacetyl-CoA. The $k_{cat}$[condensation] is 11-fold smaller than $k_{cat}$[hydrolysis], whereas the $K_m$ on acetyl-CoA is 78-fold higher than the $K_m$ on acetoacetyl-CoA (Masamune et al., 1989). The activity of thiolase PhaA on hydrolyzing acetoacetyl-CoA was previously measured to be approximately 200-fold higher than the activity of the acetoacetyl-CoA reductase PhaB on synthetically reducing acetoacetyl-CoA to form (R)-3HB-CoA (Wang et al., 2013, 2014). These findings suggests that the activity of the acetoacetyl-CoA reductase PhaB on synthetically drawing off acetoacetyl-CoA was probably the bottleneck for (R)-3HB biosynthesis.

Increasing the co-factor availability has been proven as an effective approach to improving the enzyme activity (Niederholtmeyer et al., 2010; Shen et al., 2011). NADPH, product of the photosynthesis process, is not only the driving force for carbon fixation in the Calvin cycle, but also the co-factor for the acetoacetyl-CoA reductase (PhaB1) in the (R)-3HB biosynthesis pathway (FIG. 12). Since photosynthesis activity is positively associated with the photon flux at lower range of light intensity (<200 μE/m²/s) (Williams and Laurensa, 2010; Yang et al., 2011), the next step was to cultivate strains PTrK12 and TTrK under different intensity of light in hope of stimulating the (R)-3HB production via optimizing the photosynthesis activity and the intracellular NADPH pool.

Figure 16A:
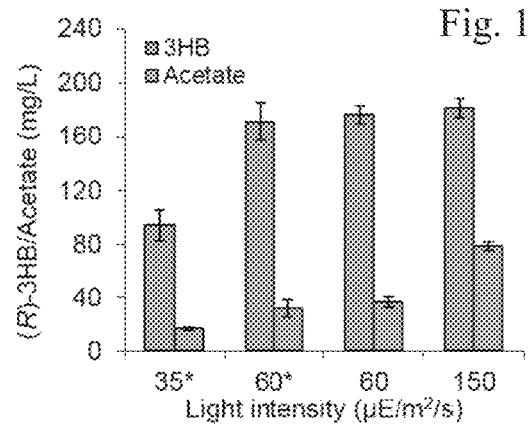
FIGS. 16A-B are (R)-3HB productions under different illumination conditions. (A) (R)-3HB and acetate produced by strains TTrK and TABd (indicated with stars). (B) (R)-3HB and acetate produced by strain PTrK12.
Figure 16B:
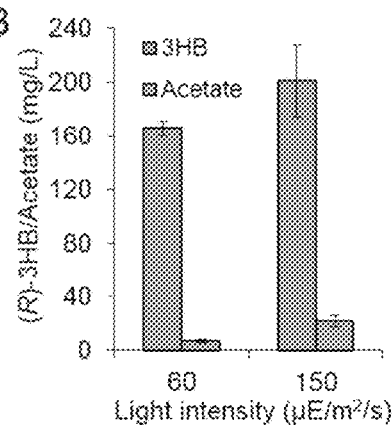

For strain TTrK (or TABd) when the light intensity was increased from 35 μE/m²/s to 60 μE/m²/s, the (R)-3HB production was elevated from 93.9 mg/L to 176.4 mg/L, nearly 2-fold increase. However, when the light intensity was further increased from 60 μE/m²/s to 150 jE/m²/s, no obvious improvement was observed in regard to the (R)-3HB productivity (FIG. 16A). In contrast, the acetate titer was increased from 16.6 mg/L to 36.5 mg/L to 78.6 mg/L when the light intensity was increased from 35 μE/m²/s to 60 μE/m²/s to 150 μE/m²/s (FIG. 16A). For strain PTrK12, the (R)-3HB productivity was increased by ~20% when the light intensity was increased from 60 μE/m²/s to 150 μE/m²/s (FIG. 16B), whereas the acetate titer was elevated to 3-fold higher, reaching 21.6 mg/L (FIG. 16B). Over all, it was found that the intracellular acetyl-CoA pool was gradually elevated with the increase of the light intensity from 35 μE/m²/s to 150 μE/m²/s which indicated increased activity of the photosynthesis, carbon fixation and probably also the intracellular NADPH abundance (FIG. 12), consistent with the literature (Williams and Laurensa, 2010; Yang et al., 2011). However, the (R)-3HB production ceased increasing with increased illumination when the light intensity surpassed 60 μE/m²/s. Based on these results, it was surmised that the expression of the acetoacetyl-CoA reductase (PhaB1) rather than supply of the co-factor NADPH was probably the rate-limiting factor for (R)-3HB production.

Multiple Copies of phaB and tesB

Figure 17A:
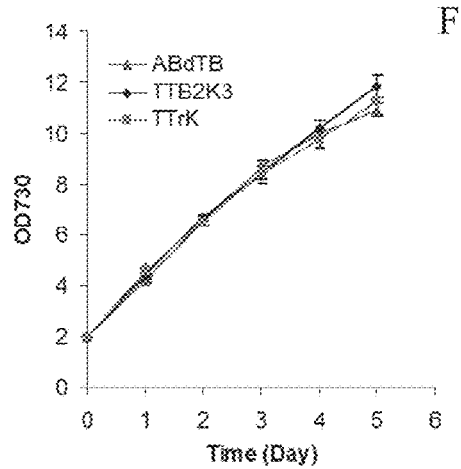
FIGS. 17A-B are a performance of *Synechocystis* strains with two copies of tesB and phaB. (A) Cell growth curve of strains TTrK, TTB2K3 and ABdTB. (B) Production of (R)-3HB and acetate.
Figure 17B:
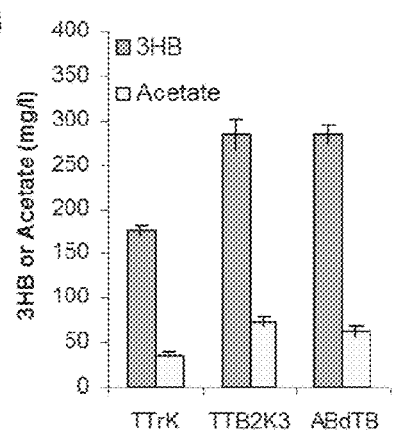

In order to increase the acetoacetyl-CoA reductase activity, gene phaB2 of *R. eutropha* H16 that encodes an isozyme of PhaB1 was de novo synthesized after codon optimization (phaB2$_{eu-opt}$), placed under the control of the P$_{tac}$ promoter and inserted into the chromosome of *Synechocystis* ABdTTe [P$_{tac}$-phaA-phaB1, P$_{tac}$-tesB, ΔphaEC]. During the genetic manipulation, the tesB gene was also codon-optimized, de novo synthesized (tesB$_{opt}$) and placed downstream of the phaB2$_{eu-opt}$ gene before being integrated into the chromosome of the *Synechocystis* ABd-TTe. The resultant strain was denominated as *Synechocystis* TTB2K3 [P$_{tac}$-phaA-phaB1, P$_{tac}$-tesB, P$_{tac}$-tesB$_{opt}$-phaB2$_{eu-opt}$, ΔphaEC] (Table 6). Strain TTB2K3 exhibited the same growth rate under illumination of 60 μE/m²/s compared to that of strain TTrK (FIG. 17A). However, the TTB2K3 strain was able to produce (R)-3HB to a titer of 285.1 mg/L after five days of cultivation, which was 1.6-fold higher than that of strain TTrK (FIG. 17B). It was also noteworthy that the acetate production by strain TTB2K3 was increased to 74.4±4.3 mg/L (vs. 41.3±4.3 mg/L for strain TTrK), probably due to the increased thioesterase activity (Table 7).

One copy of the tesB gene was then removed from the chromosome of strain TTB2K3 to construct strain ABdTB (Table 6) in order to decrease the acetate production as well as to verify if the thioesterase activity was the rate-limiting step for (R)-3HB biosynthesis. It was found that while the acetate production was decreased from 74.4 mg/L to 62.8 mg/L probably due to the decreased thioesterase activity (Table 7), strain ABdTB exhibited similar growth rate and (R)-3HB productivity compared to that of strain TTB2K3 (FIG. 17). Based on these results, we confirmed that the rate-limiting factor for (R)-3HB production in above *Synechocystis* strains was not the thioesterase (TesB) activity but instead was the acetoacetyl-CoA reductase (PhaB) activity.

Optimization of the Ribosome Binding Site for phaB1

Since the ribosome binding site (RBS) plays a crucial role in initiating the translation of the corresponding gene, the RBS for genes of interest need to be optimized in order to enhance the expression of the (R)-3HB biosynthesis genes. Previously, it was recognized that the Shine-Dalgarno (SD) sequence UAAGGAGG, which is perfectly complementary to the 3'-terminal sequence of the 16S rRNA in *Escherichia coli* K12 strain could enable 3- to 6-fold higher translation efficiency than the SD sequence AAGGA, regardless of the spacing between the SD and the translation start codon—ATG (Makrides, 1996). In this study, the RBS was examined upstream of each open reading frame of the 3HB biosynthesis relevant genes. It was found that the SD sequence upstream of the gene phaB1, AAGGAGTGG, was not a perfect match to the 3'-terminal sequence (5'-ACCUC-CUUU-3') of the 16S rRNA in *Synechocystis* 6803 (Wang et al., 2012). The original SD sequence for phaB1 was therefore replaced by sequence AAGGAGGT (RBS$_{opt}$) which is fully complementary with the 3'-terminal sequence of 16S rRNA of *Synechocystis* 6803 (FIG. 18A). The resultant strain with the RBS$_{opt}$ for gene phaB1 was denominated as R154 (Table 6).

It was found that the acetoacetyl-CoA reductase (PhaB) activity was increased by 2.2-fold in strain R154 compared to that of strain TTrK (FIG. 18B). While the growth of strain R154 exhibited a similar pattern compared to strain TTrK (FIG. 18C), strain R154 was able to produce (R)-3HB at a titer that was 1.6-fold higher than that of strain TTrK, reaching 280.2 mg/L after five days of cultivation (FIG. 18D). It suggested that the new RBS$_{opt}$ was much more efficient in initiating the translation of the gene phaB1 compared to the original RBS, and RBS optimization for genes of interest is an effective approach to enhancing the chemical production in *Synechocystis*. Further replacing the P$_{tac}$ promoter with the dual promoter P$_{psbA12}$-P$_{tac}$ for the phaA-phaB1 operon in *Synechocystis* strain R168 (Table 6) resulted in little difference in regard to the cell growth rate and the production of (R)-3HB and acetate (data not shown).

Enhanced Production of (R)-3HB from $CO_2$

Figure 20:
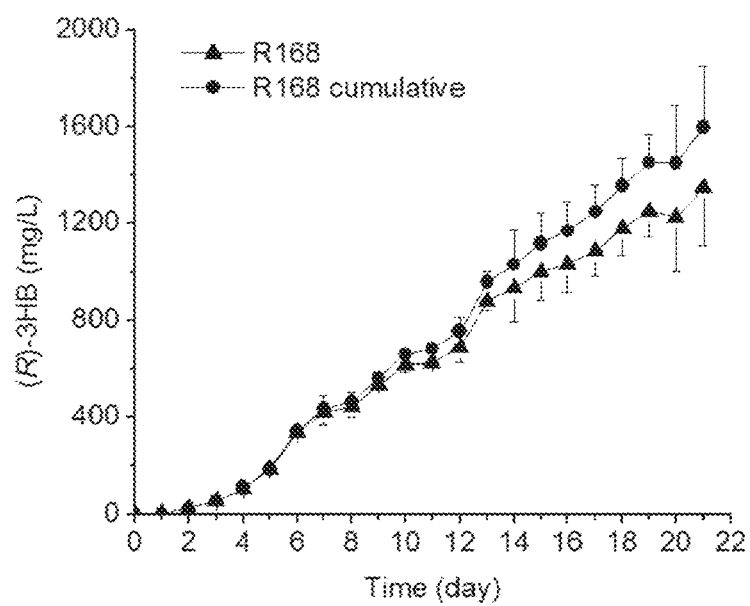
FIG. 20 is an in-flask and cumulative titers of (R)-3HB generated by strain R168.

The ability of *Synechocystis* strains to photosynthetically produce (R)-3HB directly from $CO_2$ was then examined by continuously aerating cultures with 1% $CO_2$. As shown in FIG. 19A, *Synechocystis* strains R168 and ABdTB underwent relatively fast growth during the first four to five days, and the growth rate slowed down thereafter. In contrast, the (R)-3HB production quickly accelerated after the first three to four days (FIG. 19B, FIG. 9), consistent with our previous observation (Wang et al., 2013). Starting from day 4 until day 21 (when the experiment was electively stopped), strains R168 and ABdTB exhibited average (R)-3HB production rates of ~86 and ~65 mg/L/day, respectively, with peak productivities of 208 and 139 mg/L/day, respectively. Eventually, (R)-3HB was able to accumulate in the culture medium to titers of 1347 and 987 mg/L, respectively, after 21 days of continuous cultivation (FIG. 19B). It is noteworthy that the cumulative titer of (R)-3HB was able to reach 1599 mg/L for strain R168 at the end of the cultivation (FIG. 20).

The dramatic increase of the (R)-3HB production rate compared to the previous result (Wang et al., 2013) could probably be attributed to the following reasons. First, the enzyme activity of acetoacetyl-CoA reductase, which is the bottleneck in the (R)-3HB biosynthesis pathway identified in this study (FIG. 17B, 18C), was increased by 1.5- and 2.2-fold in strains ABdTB and R154, respectively (Table 7), leading to dramatic increase of the metabolic flux towards the (R)-3HB biosynthesis. Second, as photoautotrophic growth of *Synechocystis* alkalizes the medium (Summerfield and Sherman, 2008), the pH of the culture medium increased to 10~11 when ambient air (with 0.04% $CO_2$) was aerated into the culture in the previous study (Wang et al., 2013), indicating that the $CO_2$ supply was not able to meet the demand of *Synechocystis* cells. In this study, with aerating 1% $CO_2$ into the culture, the pH of the culture medium was able to be maintained at ~8.0 during the whole cultivation process, indicating that the $CO_2$ supply was sufficient in this study. Third, in contrast to cultivation of *Synechocystis* cells by simply bubbling air into the flasks placed in a static incubator as described in the previous study (Wang et al., 2013), in this study the flasks containing *Synechocystis* cells were placed in a shaker with a rotation rate of 150 rpm during aeration, which resulted in more even distribution of the supplied $CO_2$ and photons in the cell population.

CONCLUSION

In order for cyanobacterial biotechnology to be economically feasible, chemicals of interest need to be produced at desirable high titers so that the expense in purification of unit amount of the product can be significantly reduced. To date, however, it remains a challenge to construct such a type of high-productivity cyanobacterial strains. Typically, the titers of chemicals that are photosynthetically produced by engineered cyanobacteria are below 1 g/L (Wang et al., 2012). The situation is partially due to limited well-characterized genetic tools and low level expression of the genes of interest.

Figure 15D:
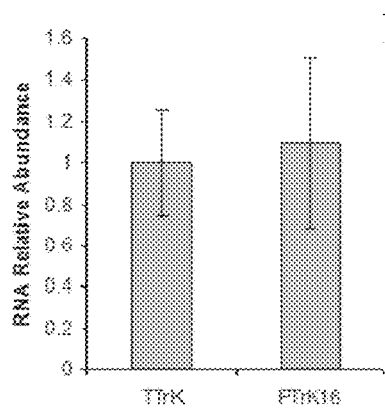
Figure 15E:
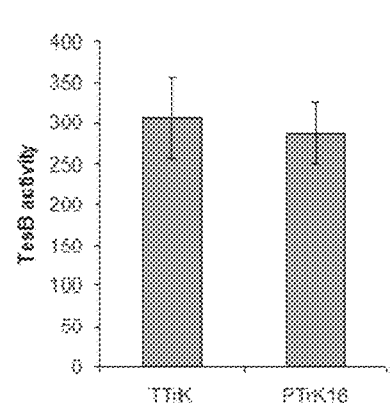

In this study, a total of six promoters were completely characterized in *Synechocystis* and it was found that the constitutive Pac promoter was the strongest in expressing the target gene under the examined experimental conditions (FIG. 14C). $P_{tac}$ and the light-inducible $P_{psbA12}$ promoter exhibited the best performance in regard to photosynthetic production of (R)-3HB (FIG. 14B). Recombination of the $P_{psbA12}$ and $P_{tac}$ to form a dual promoter resulted in approximately the same gene expression efficiency compared to that of the $P_{tac}$ promoter alone (FIG. 15C-E). The light intensity was found to be the rate-limiting factor for biosynthesis of (R)-3HB when the intensity was below 60 µE/m²/s. When the light intensity was above 60 µE/m²/s, the acetoacetyl-CoA reductase activity was found to be the rate-limiting factor. Expression of an additional copy of gene (phaB2$_{eu-opt}$) coding for acetoacetyl-CoA reductase or enhancing the translation of gene phaB1 by optimizing the RBS are both proven as effective strategies to enhance the acetoacetyl-CoA reductase enzyme activity (Table 7), resulting in 1.5- and 2.2-fold higher enzyme activity, respectively (Table 7). One of the engineered *Synechocystis* strains, R168, was able to produce and secrete (R)-3HB to the extracellular culture medium at an average rate of ~86 mg/L/day, with a peak productivity of 208 mg/L/day. The eventually achieved cumulative titer of ~1.6 g/L (FIG. 20) is to date the highest titer reported in photoautotrophic production of the hydroxyalkanoates, precursors for biodegradable plastics and fine chemicals.

It is noteworthy that without adding any organic carbon sources into the culture medium, the titer of the secreted (R)-3HB achieved in this study, ~30% dry cell weight equivalent, has reached the same level as what reported previously on cyanobacterial mixotrophic production of PHB, intracellular granules that are non-secretable (Takahashi et al., 1998; Panda and Mallick, 2007). The technology developed here thus not only has decreased the expense on culture feedstock, but also has avoided the energy-expensive cell lysis process that is necessary prior to PHB recovery, leading to an economically more desirable and "greener" technology in microbial production of (R)-3HB. Additionally, it has been demonstrated in this study that expression of genes of interest could be fine-tuned from aspects including the gene copy number, transcription, translation, light intensity and $CO_2$ supply, which are critical to improving the photosynthetic production of (R)-3HB in cyanobacterium *Synechocystis*. These strategies are applicable to improving the photosynthetic production of other chemicals in cyanobacteria.

All embodiments of any aspect of the invention can be combined with other embodiments of any aspect of the invention unless the context clearly dictates otherwise.

Various changes in the details and components that have been described may be made by those skilled in the art within the principles and scope of the invention herein described in the specification and defined in the appended claims. Therefore, while the embodiments that have been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

REFERENCES

Agrawal, G. K., Kato, H., Asayama, M., Shirai, M., 2001. An AU-box motif upstream of the SD sequence of light-dependent psbA transcripts confers mRNA instability in darkness in cyanobacteria. Nucleic Acids Res. 29, 1835-1843.

Angermayr, S. A., Hellingwerf, K. J., 2013. On the use of metabolic control analysis in the optimization of cyanobacterial biosolar cell factories. J. Phys. Chem. B 117, 11169-11175.

Angermayr, S. A., Paszota, M., Hellingwerf, K. J., 2012. Engineering a cyanobacterial cell factory for production of lactic acid. Appl. Environ. Microbiol. 78, 7098-7106.

Dexter, J., Fu, P., 2009. Metabolic engineering of cyanobacteria for ethanol production. Energ. Environ. Sci. 2, 857-864.

Elhai, J., 1993. Strong and regulated promoters in the cyanobacterium *Anabaena* PCC 7120. FEMS Microbiol. Lett. 114, 179-184.

Eriksson, J., Salih, G. F., Ghebramedhin, H., Jansson, C., 2000. Deletion mutagenesis of the 5' psbA2 region in *Synechocystis* 6803: identification of a putative cis element involved in photoregulation. Mol. Cell Biol. Res. Commun. 3, 292-198.

Gao, W., Zhang, W., Meldrum, D. R., 2011. RT-qPCR based quantitative analysis of gene expression in single bacterial cells. J. Microbiol. Methods 85, 221-227.

Gao, Z., Zhao, H., Li, Z., Tan, X. and Lu, X., 2012. Photosynthetic production of ethanol from carbon dioxide in genetically engineered cyanobacteria. Energy Environ. Sci. 5, 9857-9865.

Golden, S. S., 1995. Light-responsive gene expression in cyanobacteria. J. Bacteriol. 177, 1651-1654.

Guerrero, F., Carbonell, V., Cossu, M., Correddu, D., Jones, P. R., 2012. Ethylene synthesis and regulated expression of recombinant protein in *Synechocystis* sp. PCC 6803. PLoS ONE 7, e50470.

Horie, Y., Ito, Y., Ono, M., Moriwaki, N., Kato, H., Hamakubo, Y., Amano, T., Wachi, M., Shirai, M., Asayama, M., 2007. Dark-induced mRNA instability involves RNase E/G-type endoribonuclease cleavage at the AU-box and SD sequences in cyanobacteria. Mol. Genet. Genomics 278, 331-346.

Huang, H. H., Camsund, D., Lindblad, P., Heidorn, T., 2010. Design and characterization of molecular tools for a Synthetic Biology approach towards developing cyanobacterial biotechnology. Nucleic Acids Res. 38, 2577-2593.

Liu, X., Sheng, J., Curtiss, R. 3rd., 2011. Fatty acid production in genetically modified cyanobacteria. Proc. Natl. Acad. Sci. U.S.A. 108, 6899-6904.

Ludwig, M., Bryant, D. A., 2011. Transcription profiling of the model cyanobacterium *Synechococcus* sp. strain PCC 7002 by Next-Gen (SOLiD™) Sequencing of cDNA. Front. Microbiol. 2, 41.

Makrides, S. C., 1996. Strategies for achieving high-level expression of genes in *Escherichia coli*. Microbiol. Rev. 60, 512-538.

Marraccini, P., Bulteau, S., Cassier-Chauvat, C., Mermet-Bouvier, P., Chauvat, F., 1993. A conjugative plasmid vector for promoter analysis in several cyanobacteria of the genera *Synechococcus* and *Synechocystis*. Plant Mol. Biol. 23, 905-909.

Masamune, S., Walsh, C. T., Sinskey A. J. and Peoples, O. P., 1989. Poly-(R)-3-hydroxybutyrate (PHB) biosynthesis: mechanistic studies on the biological Claisen condensation catalyzed by β-ketoacyl thiolase. Pure Appl. Chem., 61, 303-312.

Mohamed, A., Jansson, C., 1989. Influence of light on accumulation of photosynthesis-specific transcripts in the cyanobacterium *Synechocystis* 6803. Plant Mol. Biol. 13, 693-700.

Mohamed, A., Eriksson, J., Osiewacz, H. D., Jansson, C., 1993. Differential expression of the psbA genes in the cyanobacterium *Synechocystis* 6803. Mol. Gen. Genet. 238, 161-168.

Nair, U., Thomas, C., Golden, S. S., 2001. Functional elements of the strong psbAI promoter of *Synechococcus elongatus* PCC 7942. J. Bacteriol. 183, 1740-1747.

Niederholtmeyer, H., Wolfstadter, B., Savage, D., Silver, P., Way, J., 2010. Engineering cyanobacteria to synthesize and export hydrophilic products. Appl. Environ. Microb. 76, 3462-3466.

Oliver, J. W., Machado, I. M., Yoneda, H., Atsumi, S., 2014. Combinatorial optimization of cyanobacterial 2,3-butanediol production. Metab. Eng. 22, 76-82.

Panda, B., Mallick, N., 2007. Enhanced poly-beta-hydroxybutyrate accumulation in a unicellular cyanobacterium, *Synechocystis* sp. PCC 6803. Lett. Appl. Microbiol. 44, 194-198.

Qi, F., Yao, L., Tan, X., Lu, X., 2013. Construction, characterization and application of molecular tools for metabolic engineering of *Synechocystis* sp. Biotechnol. Lett. 35, 1655-1661.

Rippka, R., Deruelles, J., Waterbury, J. B., Herdman, M., Stanier, R. Y., 1979. Generic assignments, strain histories and properties of pure cultures of cyanobacteria. J. Gen. Microbiol. 111, 1-61.

Sakurai, I., Stazic, D., Eisenhut, M., Vuorio, E., Steglich, C., Hess, W. R., Aro, E. M., 2012. Positive regulation of psbA gene expression by cis-encoded antisense RNAs in *Synechocystis* sp. PCC 6803. Plant Physiol. 160, 1000-1010.

Salis, H. M., Mirsky, E. A., Voigt, C. A., 2009. Automated design of synthetic ribosome binding sites to control protein expression. Nat. Biotechnol. 27, 946-950.

Shen, C. R., Lan, E. I., Dekishima, Y., Baez, A., Cho, K. M., Liao, J. C., 2011. Driving forces enable high-titer anaerobic 1-butanol synthesis in *Escherichia coli*. Appl. Environ. Microbiol. 77, 2905-2915.

Summerfield, T., Sherman, L., 2008. Global transcriptional response of the alkali-tolerant cyanobacterium *Synechocystis* sp. strain PCC 6803 to a pH 10 environment. Appl. Environ. Microbiol. 74, 5276-5284.

Takahashi, H., Miyake, M., Tokiwa, Y., Asada, Y., 1998. Improved accumulation of poly-3-hydroxybutyrate by a recombinant cyanobacterium. Biotechnol. Lett. 20, 183-186.

Tseng, H. C., Martin, C. H., Nielsen, D. R., Prather, K. L., 2009. Metabolic engineering of *Escherichia coli* for enhanced production of (R)- and (S)-3-hydroxybutyrate. Appl. Environ. Microbiol. 75, 3137-3145.

Ungerer, J., Tao, L., Davis, M., Ghirardi, M., Maness, P. C. and Yu, J., 2012. Sustained photosynthetic conversion of $CO_2$ to ethylene in recombinant cyanobacterium *Synechocystis* 6803. Energy Environ. Sci. 5, 8998-9006.

Wang, B., Wang, J., Zhang, W., Meldrum, D. R., 2012. Application of synthetic biology in cyanobacteria and algae. Front. Microbiol. 3, 344.

Wang, B., Pugh, S., Nielsen, D. R., Zhang, W., Meldrum, D. R., 2013. Engineering cyanobacteria for photosynthetic production of 3-hydroxybutyrate directly from $CO_2$. Metab. Eng. 16, 68-77.

Wang, B., Pugh, S., Nielsen, D. R., Zhang, W., Meldrum, D. R., 2014. Corrigendum to "Engineering cyanobacteria for photosynthetic production of 3-hydroxybutyrate directly from $CO_2$" [Metab. Eng. 16 (2013) 68-77]. Metab. Eng. 21, 1.

Williams, P. J. le B. and Laurensa, L. M. L. Microalgae as biodiesel & biomass feedstocks: Review & analysis of the biochemistry, energetics & economics. Energy Environ. Sci. 3, 554-590.

Xu, Y., Alvey, R. M., Byrne, P. O., Graham, J. E., Shen, G., Bryant, D. A. Expression of genes in cyanobacteria: Adaptation of endogenous plasmids as platforms for high-level gene expression in *Synechococcus* sp. PCC 7002. In: Carpentier, R., ed. Photosynthesis Research Protocols. New York, N.Y.: Springer, 2011:684.

Yang, T., Lyons, S., Aguilar, C., Cuhel, R., Teske, A., 2011. Microbial communities and chemosynthesis in yellowstone lake sublacustrine hydrothermal vent waters. Front. Microbiol. 2, 130.

We claim:

1. A method of photosynthetic production of 3-hydroxybutyrate comprising culturing a *Synechocystis* cyanobacterium under conditions to produce said 3-hydroxybutyrate;

wherein said *Synechocystis* cyanobacterium is genetically engineered to overexpress the gene phaA2 and one or more of the genes phaB2, phaA, phaB, thil, hbd, and tesB and wherein the genes phaC and phaE have been inactivated or deleted; or wherein said *Synechocystis* cyanobacterium is genetically engineered to overexpress the gene phaA2 and at least one of a phaA or a thil gene, at least one of a phaB or hbd gene, and a tesB gene, and wherein the genes phaC and phaE have been inactivated or deleted.

2. The method of claim 1, wherein solar energy is the sole energy source during said culturing.

3. The method of claim 1, wherein bicarbonate or CO2 is the sole carbon source during said culturing.

4. The method of claim 1, wherein carbonate is the sole carbon source during said culturing.

5. The method of claim 1, additionally comprising the step of multi-cycle production of 3-hydroxybutyrate by culture medium exchange.

6. The method of claim 1, wherein 3-hydroxybutyrate production titers exceed 100 mg/l of *Synechocystis* culture.

7. The method of claim 1, wherein 3-hydroxybutyrate production titers exceed 200 mg/l of *Synechocystis* culture.

8. The method of claim 1, wherein said 3-hydroxybutyrate is secreted.

9. The method of claim 1, wherein said cyanobacterium is *Synechocystis* sp. PCC 6803.

* * * * *

UNITED STATES PATENT AND TRADEMARK OFFICE
CERTIFICATE OF CORRECTION

PATENT NO. : 10,246,726 B2  
APPLICATION NO. : 15/938742  
DATED : April 2, 2019  
INVENTOR(S) : Bo Wang et al.

Page 1 of 1

It is certified that error appears in the above-identified patent and that said Letters Patent is hereby corrected as shown below:

In the Claims

Claim 1, Line 6, "phaA2" should read --*phaA2*--

Claim 1, Line 7, "phaB2, phaA, phaB, thil, hbd," should read --*phaB2, phaA, phaB, thil, hbd,*--

Claim 1, Line 8, "tesB and wherein the genes phaC and phaE have been" should read --*tesB* and wherein the genes *phaC* and *phaE* have been--

Claim 1, Line 11, "phaA2" should read --*phaA2*--

Claim 1, Line 12, "one of a phaA or a thil gene, at least one of a phaB or" should read --one of a *phaA* or a *thil* gene, at least one of a *phaB* or--

Claim 1, Line 13, "hbd gene, and a tesB gene, and wherein the genes phaC" should read --*hbd* gene, and a *tesB* gene, and wherein the genes *phaC*--

Claim 1, Line 14, "phaE" should read --*phaE*--

Claim 3, Line 17, "CO2" should read --$CO_2$--

Signed and Sealed this  
Second Day of July, 2019

Andrei Iancu  
*Director of the United States Patent and Trademark Office*